United States Patent [19]
June et al.

[11] Patent Number: 6,143,291
[45] Date of Patent: Nov. 7, 2000

[54] METHODS FOR MODULATING T CELL SURVIVAL BY MODULATING BCL-$X_L$ PROTEIN LEVEL

[76] Inventors: Carl H. June, 7 Harlow Ct., Rockville, Md. 20850; Craig B. Thompson, 1375 E. 57th St., Chicago, Ill. 60637

[21] Appl. No.: 08/481,739

[22] Filed: Jun. 7, 1995

Related U.S. Application Data

[63] Continuation-in-part of application No. 08/435,518, May 4, 1995, abandoned.

[51] Int. Cl.[7] .............................. A61K 48/00; C12N 5/10; C12N 15/09
[52] U.S. Cl. ................... 424/93.21; 435/375; 435/320.1; 435/172.3
[58] Field of Search .......................... 435/320.1, 6, 69.1, 435/172.3, 375; 514/44; 935/62, 55–57, 34, 33; 424/93.2

[56] References Cited

FOREIGN PATENT DOCUMENTS

WO 95/00642   1/1995   WIPO .

OTHER PUBLICATIONS

Strasser A. et al.,"bcl–2 Transgene Inhibits T Cell Death and Perturbs Thymic Self–Censorship", *Cell*, vol. 67, pp. 889–899 (1991).
Culver et al. "Gene Therapy for Cancer," TIG, vol. 10(5): 174–178, 1994.
Marshall, E. "Gene Therapy's Growing Pains," Science, vol. 269: 1050–1055, Aug. 25, 1995.
Miller et al. "Targeted Vectors for Gene Therapy," FASEB, vol. 9: 190–199, Feb. 1995.
Hodgson et al. "Advances in vector systems for Gene Therapy," Exp. Opin. Ther. Patents, vol. 5(5): 459–468, 1995.
Dole et al. "bcl–xl and bclx–s Modulate apoptosis in Neuroblastoma," Blood, vol. 84(10): 373a, Abstract #1477, 1994.
Boise, L., et al., "bcl–x, a bcl–2–Related Gene that Functions as a Dominant Regulator of Apoptotic Cell Death" *Cell*, vol. 74, 597–608 (1993).
Cory, S., "Regulation of Lymphocyte Survival by the BCL–2 Gene Family," *Annu. Rev. Immunol.* vol. 13, 513–543 (1995).
Fang, W., et al., "Cloning and Molecular Characterization of Mouse bcl–x in B and T Lymphocytes," *The Journal of Immunology*, vol. 153, 4388–4398 (1994).
González–Garcia, M., et al., "bcl–$x_L$ is the Major bcl–x mRNA Form Expressed During Murine Development and its Product Localizes to Mitochondria,"*Development*, vol. 120, 3033–3042 (1994).
Gottschalk, A., et al., "Identification of Immunosuppressant–Induced Apoptosis in a Murine B–Cell Line and its Prevention by bcl–x but not bcl–2," *Proc. Natl. Acad. Sci. USA*, vol. 91, 7350–7354 (1994).
Lowenthal, J. and Harris, A., "Activation of Mouse Lymphocytes Inhibits Induction of Rapid Cell Death by X–Irradiation," *The Journal of Immunology*, vol. 135, No. 2, 1119–1125 (1985).
Martin, S. and Green, D., "Apoptosis and Cancer: The Failure of Controls on Cell Death and Cell Survival," *Critical Reviews in Oncology/Hematology*, vol. 18, 137–153 (1995).
Michaud, G., et al., "Expression of BCL–X in T Cell Ontogeny,"*Blood*, vol. 84, No. 10, p. 286a, Abstract # 1129 (1994).
Motoyama, N., et al., "Massive Cell Death of Immature Hematopoietic Cells and Neurons in Bcl–x–Defecient Mice," *Science*, vol. 267, 1506–1510 (1995).
Nuñez, G. and Gonzalez–Garcia, M., "BCL–X, A Dominant Regulator of Apoptotic Cell Death," *FASEB J.*, vol. 8, No. 5, p. A807, Abstract # 4678 (1994).
Nuñez, G., et al., "Bcl–2 and Bcl–x: Regulatory Switches for Lymphoid Death and Survival," *Immunology Today*, vol. 15, No. 12, 582–588 (1994).
Osborne, B., "Induction of Genes During Apoptosis: Examples From the Immune System," *Seminars in Cancer Biology*, vol. 6, 27–33 (1995).
Savill, J., "Apoptosis in Disease," *European Journal of Clinical Investigation*, vol. 24, 715–723 (1994).
Yang, E., et al., "Bad, a Heterodimeric Partner for Bcl–$x_L$ and Bcl–2, Displaces Bax and Promotes Cell Death," *Cell*, vol. 80, 285–291 (1995).
Yang, E., et al., "Bad, a New BCL–2 Family Member, Heterodimerizes with BCL–2 and BCL–$x_L$ in Vivo, and Promotes Cell Death," *Blood*, vol. 84, No. 10, p. 373a, Abstract # 1476 (1994).

*Primary Examiner*—Karen M. Hauda
*Attorney, Agent, or Firm*—Lahive & Cockfield, LLP

[57] ABSTRACT

Methods for protecting a T cell from cell death are described. The methods involve contacting the T cell with an agent which augments the bcl-$X_L$ protein level in the T cell such that it is protected from cell death. The invention further pertains to methods for increasing the susceptibility of a T cell to cell death, comprising contacting the T cell with at least one agent which decreases bcl-$X_L$ protein level in the T cell. Both in vivo and in vitro methods are described.

5 Claims, 13 Drawing Sheets

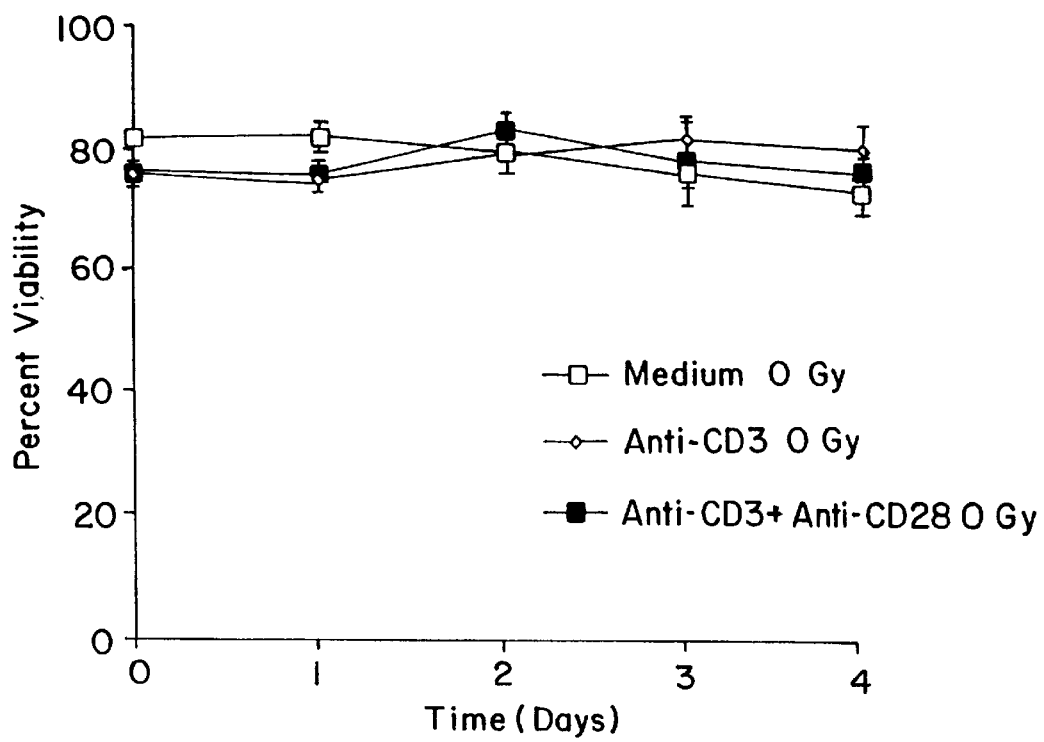
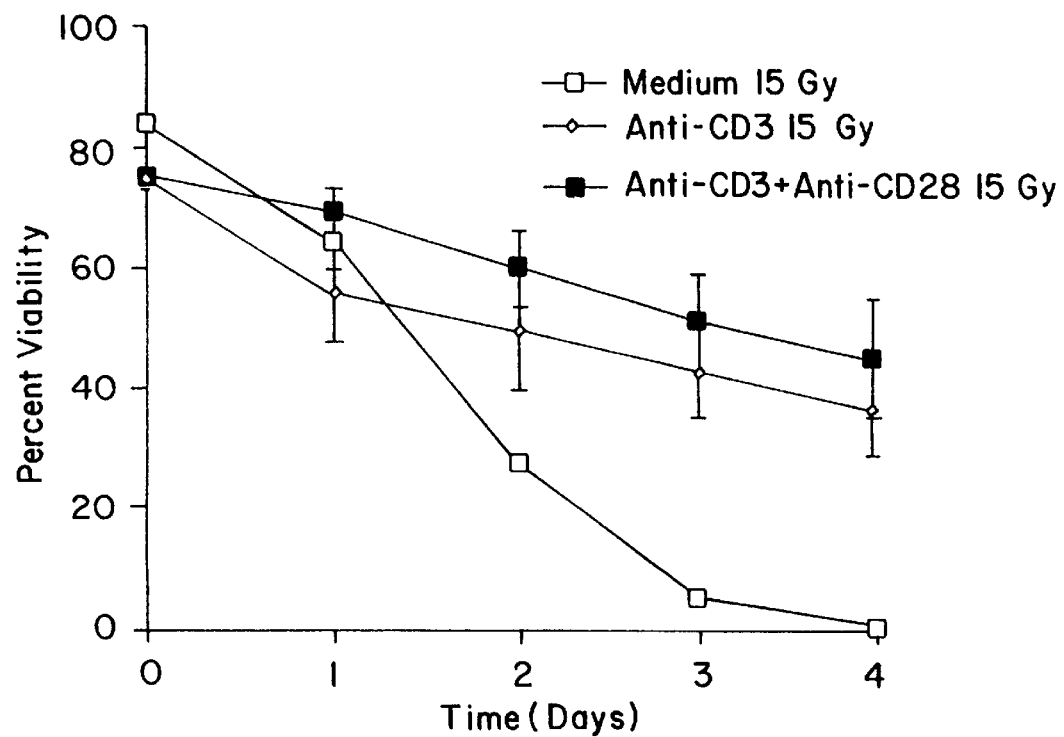

RNA bcl-x bcl-2

HLA

```
                        SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 926 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 135..836

(xi) SEQUENCE DESCRIPTION: SEQ ID NO:1:

GAATCTCTTT CTCTCCCTTC AGAATCTTAT CTTGGCTTTG GATCTTAGAA GAGAATCACT         60

AACCAGAGAC GAGACTCAGT GAGTGAGCAG GTGTTTTGGA CAATGGACTG GTTGAGCCCA        120

TCCCTATTAT AAAA ATG TCT CAG AGC AAC CGG GAG CTG GTG GTT GAC TTT          170
              Met Ser Gln Ser Asn Arg Glu Leu Val Val Asp Phe
                1               5                   10

CTC TCC TAC AAG CTT TCC CAG AAA GGA TAC AGC TGG AGT CAG TTT AGT          218
Leu Ser Tyr Lys Leu Ser Gln Lys Gly Tyr Ser Trp Ser Gln Phe Ser
        15                  20                  25

GAT GTG GAA GAG AAC AGG ACT GAG GCC CCA GAA GGG ACT GAA TCG GAG          266
Asp Val Glu Glu Asn Arg Thr Glu Ala Pro Glu Gly Thr Glu Ser Glu
    30                  35                  40

ATG GAG ACC CCC AGT GCC ATC AAT GGC AAC CCA TCC TGG CAC CTG GCA          314
Met Glu Thr Pro Ser Ala Ile Asn Gly Asn Pro Ser Trp His Leu Ala
45                  50                  55                  60

GAC AGC CCC GCG GTG AAT GGA GCC ACT GGC CAC AGC AGC AGT TTG GAT          362
Asp Ser Pro Ala Val Asn Gly Ala Thr Gly His Ser Ser Ser Leu Asp
                65                  70                  75

GCC CGG GAG GTG ATC CCC ATG GCA GCA GTA AAG CAA GCG CTG AGG GAG          410
Ala Arg Glu Val Ile Pro Met Ala Ala Val Lys Gln Ala Leu Arg Glu
            80                  85                  90

GCA GGC GAC GAG TTT GAA CTG CGG TAC CGG CGG GCA TTC AGT GAC CTG          458
Ala Gly Asp Glu Phe Glu Leu Arg Tyr Arg Arg Ala Phe Ser Asp Leu
        95                  100                 105

ACA TCC CAG CTC CAC ATC ACC CCA GGG ACA GCA TAT CAG AGC TTT GAA          506
Thr Ser Gln Leu His Ile Thr Pro Gly Thr Ala Tyr Gln Ser Phe Glu
    110                 115                 120
```

```
CAG GTA GTG AAT GAA CTC TTC CGG GAT GGG GTA AAC TGG GGT CGC ATT      554
Gln Val Val Asn Glu Leu Phe Arg Asp Gly Val Asn Trp Gly Arg Ile
125                 130                 135                 140

GTG GCC TTT TTC TCC TTC GGC GGG GCA CTG TGC GTG GAA AGC GTA GAC      602
Val Ala Phe Phe Ser Phe Gly Gly Ala Leu Cys Val Glu Ser Val Asp
                145                 150                 155

AAG GAG ATG CAG GTA TTG GTG AGT CGG ATC GCA GCT TGG ATG GCC ACT      650
Lys Glu Met Gln Val Leu Val Ser Arg Ile Ala Ala Trp Met Ala Thr
            160                 165                 170

TAC CTG AAT GAC CAC CTA GAG CCT TGG ATC CAG GAG AAC GGC GGC TGG      698
Tyr Leu Asn Asp His Leu Glu Pro Trp Ile Gln Glu Asn Gly Gly Trp
        175                 180                 185

GAT ACT TTT GTG GAA CTC TAT GGG AAC AAT GCA GCA GCC GAG AGC CGA      746
Asp Thr Phe Val Glu Leu Tyr Gly Asn Asn Ala Ala Ala Glu Ser Arg
    190                 195                 200

AAG GGC CAG GAA CGC TTC AAC CGC TGG TTC CTG ACG GGC ATG ACT GTG      794
Lys Gly Gln Glu Arg Phe Asn Arg Trp Phe Leu Thr Gly Met Thr Val
205                 210                 215                 220

GCC GGC GTG GTT CTG CTG GGC TCA CTC TTC AGT CGG AAA TGACCAGACA       843
Ala Gly Val Val Leu Leu Gly Ser Leu Phe Ser Arg Lys
                225                 230

CTGACCATCC ACTCTACCCT CCCACCCCCT TCTCTGCTCC ACCACATCCT CCGTCCAGCC    903

GCCATTGCCA CCAGGAGAAC CCG                                            926

(2) INFORMATION FOR SEQ ID NO:2:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
                20                  25                  30

Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
        50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190
```

```
Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGAGATATAC ATATGTCTCA GAGCAACCGG GAGCTGGTG                              39

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CGGGATCCCG TCATTTCCGA CTGAAGAGTG AGCCCAGCAG                             40
```

METHODS FOR MODULATING T CELL SURVIVAL BY MODULATING BCL-$X_L$ PROTEIN LEVEL

RELATED APPLICATIONS

This application is a continuation in part of U.S. application Ser. No. 08/435,518 filed May 4, 1995, abandoned, entitled "Methods for Enhancing T Cell Survival by Augmenting bcl-$X_L$ Protein Level", now abandoned. The entire contents of the aforementioned application and all references, issued patents, and published patent applications cited therein are incorporated herein by reference.

GOVERNMENT SUPPORT

Work described herein was supported in part by NIH grant PO1 AI35294, and NMRDC grant 61153N AE.4120.001.1402. The U.S. government therefore may have certain rights in the invention.

BACKGROUND OF THE INVENTION

The control of peripheral T cell survival is critical to the maintenance of an effective peripheral immune repertoire. Some aspects of T cell survival appear to be linked to the state of T cell activation. T cell activation is initiated by the engagement of the T cell receptor/CD3 complex (TCR/CD3) by a peptide-antigen bound to a major histocompatibility complex (MHC) molecule on the surface of an antigen-presenting cell (APC) (Schwartz, R. H. (1990) Science 248, 1349). While this is the primary signal in T cell activation, other receptor-ligand interactions between APCs and T cells are required for complete activation. For example, TCR stimulation in the absence of other molecular interactions can induce a state of anergy, such that these cells can not respond to full activation signals upon restimulation (Schwartz, R. H. (1990) Science 248, 1349; Harding, F. A., McArthur J. G., Gross, J. A., Raulet, D. H., and Allison, J. P. (1992). Nature 356, 607.). Alternatively, T cells have been shown to die by programmed cell death (PCD) when activated by TCR engagement alone (Webb, S., Morris, C., and Sprent, J. (1990) Cell 63, 1249; Kawabe, Y., and Ochi, A. (1991) Nature 349, 245; Kabelitz, D., and Wesselborg, S. (1992) Int. Immunol 4, 1381; Groux, H., Monte, D., Plouvier, B., Capron, A., and Ameisen, J-C (1993). Eur. J. Immunol. 23, 1623).

There are multiple receptor-ligand interactions which take place between the T cell and the APC. Many interactions are adhesive in nature and reinforce the contact between the two cells (Springer, T. A., Dustin, M. L., Kishimoto, T. K., and Marlin, S. D. (1987) Annul. Rev. Immunol. 5, 223), while other interactions transduce additional activation signals to the T cell (Bierer, B. E., and Burakoff, S. J. (1991) Adv. Cancer Res. 56, 49). CD28, a surface glycoprotein present on 80% of peripheral T cells in humans, has been shown to be an important costimulatory receptor (June, C. H., Bluestone, J. A., Nadler, L. M. and Thompson, C. B. (1994) Immunol. Today 15, 321; Linsley, P. S. Ledbetter, J. A. (1993) Annu. Rev. Immunol. 11, 191). A costimulatory signal is transduced through CD28 when T cells encounter an antigen-presenting cell expressing either of the CD28 ligands B7-1 or B7-2.

Costimulation of T cells has been shown to affect multiple aspects of T cell activation (June, C. H., Bluestone, J. A., Nadler, L. M. and Thompson, C. B. (1994) Immunol. Today 15, 321). Costimulation will lower the concentration of anti-CD3 required to induce a proliferative response in culture (Gimmi, C. D, Freeman, G. J., Gribben, J. G., Sugita, K., Freedman, A. S., Morimoto, C., and Nadler, L. M. (1991). Proc. Natl. Acad. Sci. USA 88, 6575). CD28 costimulation also markedly enhances the production of lymphokines by helper T cells through transcriptional and post-transcriptional regulation of gene expression Lindsten, T., June, C. H., Ledbetter, J. A., Stella, G., and Thompson, C. B. (1989) Science 244, 339; Fraser, J. D., Irving, B. A., Crabtree, G. R., and Weiss, A. (1991) Science 251, 313), and can activate the cytolytic potential of cytotoxic T cells. Inhibition of CD28 costimulation in vivo can block xenograft rejection and allograft rejection is significantly delayed (Lenschow, D. J., Zeng, Y., Thistlethwaite, J. R., Montag, A., Brady, W., Gibson, M. G., Linsley, P. S., and Bluestone, J. A. (1992) Science 257, 789; Turka, L. A., Linsley, P. S., Lin, H., Brady, W., Leiden, J. M., Wei, R-Q., Gibson, M. L., Zheng, X-G., Mydral, S., Gordon, D., Bailey, T., Bolling, S. F., and Thompson, C. B. (1992) Proc. Natl. Acad. Sci. USA 89, 11102). In addition, transfection of B7 into a tumor cell line facilitates recognition and prevention of tumor growth (Chen, L., Ashe, S., Brady, W. A., Hellstrom, I., Hellstrom, K. E., Ledbetter, J. A., McGowan, P., and Linsley P. S. (1992) Cell 71, 1093; Townsend, S. E., and Allison, J. P. (1993) Science 259, 368).

Until recently, relatively little has been known about how peripheral T cell survival is controlled. Studies suggest that mitogen-activation of T cells enhances their resistance to programmed cell death (PCD) initiated by treatment with such agents as radiation (Schrek, R., and Stefani, S. (1964) J. Nat. Cancer Inst. 32, 507; Lowenthal, J. W. and Harris, A. W. (1985) J. Immunol. 135, 1119; Stewart, C. C., Stevenson, A. P., and Habbersett, R. C. (1988) J. Radiat. Biol. 53, 77). In contrast, T cell activation through the TCR alone has been reported to increase the susceptibility of T cells to undergo PCD (Kabelitz, D., and Wesselborg, S. (1992) Int. Immunol 4, 1381; Groux, H., Monte, D., Plouvier, B., Capron, A., and Ameisen, J-C (1993). Eur. J. Immunol. 23, 1623).

Recently, several genes have been identified that appear to play roles in regulating T cell survival. The survival of quiescent lymphocytes in the mouse is dependent on the expression of the bcl-2 gene (Nakayama, K-I., Nakayama, K., Negishi, I., Kuida, K., Shinkai, Y., Louie, M. C. Fields, L. E., Lucas, P. J. Stewart, V., Alt, F. W., and Loh, D. Y. (1993) Science 261, 1584). Animals deficient in the bcl-2 gene have T cells with an increased susceptibility to undergo PCD when placed in culture. Bcl-2-deficient animals become profoundly lymphopenic within the first few weeks of life (Veis, D. J., Sorenson, C. M., Shutter, J. R., and Korsmeyer, S. J. (1993a) Cell 75, 229). In contrast, animals with mutations in the Fas cell surface receptor fail to clear the excess immune cells generated in the course of an immune response (Watanabe-Fukunaga, R., Brannan, C. I., Copeland, N. G., Jenkins, N. A., and Nagata, S. (1992) Nature 356, 314). Fas-deficient animals ultimately develop profound autoimmune disease. These data suggest that T cell survival may be as tightly regulated as T cell proliferation.

Inappropriate regulation of T cell death may result in immune system disorders (e.g., immunodeficiencies or autoimmunity). Moreover, infection of T cells with certain infectious microorganisms results in killing of the T cells. In particular, infection of T cells with human immunodeficiency virus (HIV) results in cell death induced by programmed cell death (Gougon, M.-L. and Montagnier, L. (1993) Science 260, 1269). Thus, methods for controlling T cell death and in particular inhibiting such death, are needed.

SUMMARY

The present invention provides methods for modulating T cell survival, and in particular for protecting a T cell from cell death. The methods of the invention are based, at least in part, on the discovery that T cell costimulation (e.g., through CD28) results in increased production of the protein bcl-$X_L$ in the T cell and enhanced T cell survival. Moreover, increased production of bcl-$X_L$ protein in T cells by other means (eg., transfection of a bcl-$X_L$ gene into the T cells) also results in enhanced T cell survival. Accordingly, to protect a T cell from death, according to the methods of the invention, the amount of bcl-$X_L$ protein in the T cell is increased such that T cell survival is enhanced.

In one embodiment, T cell survival is enhanced by contacting the T cell with an agent which increases bcl-$X_L$ protein level. In a preferred embodiment of the method, bcl-$X_L$ protein level in a T cell is augmented by introducing into the T cell a nucleic acid encoding a bcl-$X_L$ protein. In another embodiment of the method, bcl-$X_L$ protein levels in a T cell is augmented by contacting the T cell with an agent which acts intracellularly to increase endogenous bcl-$X_L$ protein levels. Another preferred agent which increases bcl-$X_L$ protein level is an agent which interacts with a molecule on the surface of the T cell. The method of the invention is useful for treating disorders or conditions associated with increased or inappropriate T cell death, such as T cell infection with HIV. The method is also useful for enhancing T cell survival to thereby stimulate an immune reaction, for example to accelerate elimination of a pathogenic microorganism.

The present invention also pertains to methods for inducing T cell death or for rendering a T cell susceptible to cell death. These methods involve contacting the T cell with an agent which decreases the level of bcl-$X_L$ protein in the T cell. In a preferred embodiment the agent prevents induction of bcl-$X_L$ protein. These methods are useful for downregulating immune reactions.

BRIEF DESCRIPTION OF THE DRAWINGS

FIG. 1A–B is a graphical representation of the percent viability of CD28+T cells at 1, 2, 3, 4, and 5 days following incubation of the T cells for 12 hours in medium alone (open squares), in the presence of anti-CD3 (closed diamonds), or in the presence of anti-CD3 and anti-CD28 (closed squares) prior to γ-irradiation (panel B) or left untreated (panel A).

FIG. 7 panel C is a photograph of a Western blot showing the amount of bcl-$X_L$ protein in the Jurkat clones transfected with a bcl-$X_L$ expression plasmid (bcl-$X_L$ clones 1, 2, and 3) or control plasmid (Neo clones 1, 2, and 3).

FIG. 7 panel D is a graphical representation of the percent survival of CTLL-2 cell clones transfected with a bcl-$X_L$ expression plasmid (CTLL-2 bcl-$X_L$ clones 1 and 2) or non transfected (CTLL-2) at 0, 12, 24, 36, and 48 hours following IL-2 withdrawal.

FIG. 7 Panel E is a photograph of a Western blot showing the amount of bcl-$X_L$ protein in the CTLL-2 cell clones transfected with a bcl-$X_L$ expression plasmid (CTLL-2 bcl-$X_L$ clones 1 and 2) or non transfected (CTLL-2).

DETAILED DESCRIPTION

Figure 2A:
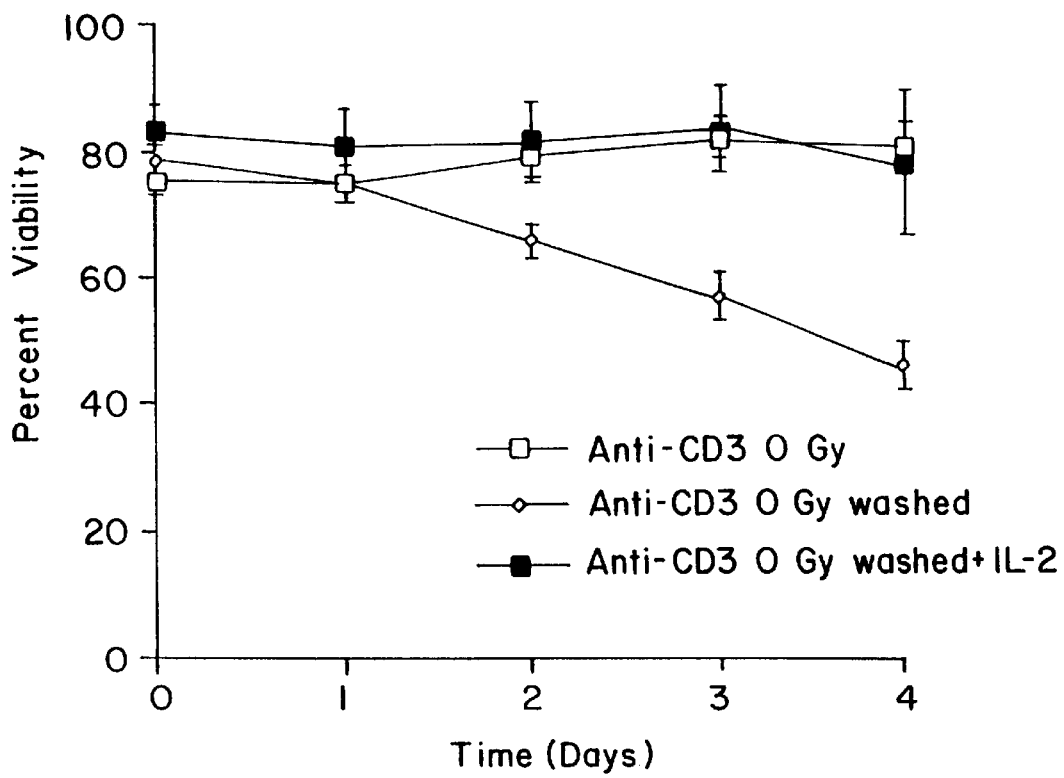
FIGS. 2 A–D are graphical representations of the percent viability of CD28+T cells at 1, 2, 3, 4, and 5 days following incubation of the T cells for 12 hours with anti-CD3 alone (panels A and B) or with anti-CD3 and anti-CD28 (panels C and D) and then either left in their conditioned medium (open squares), washed and resuspended in fresh medium (open diamonds), or washed and resuspended in fresh medium supplemented with 200 U/ml of rIL-2 (closed squares) prior to γ-irradiation (panels B and D) or left untreated (panel A and C).
Figure 2B:
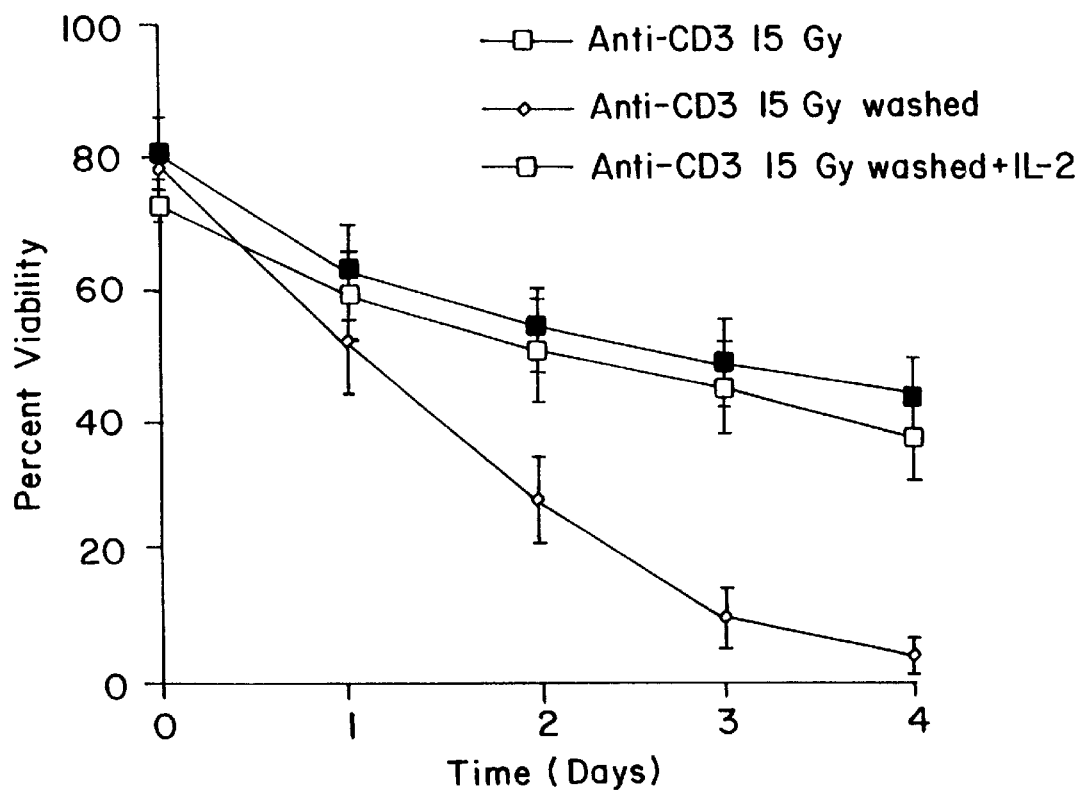
Figure 2C:
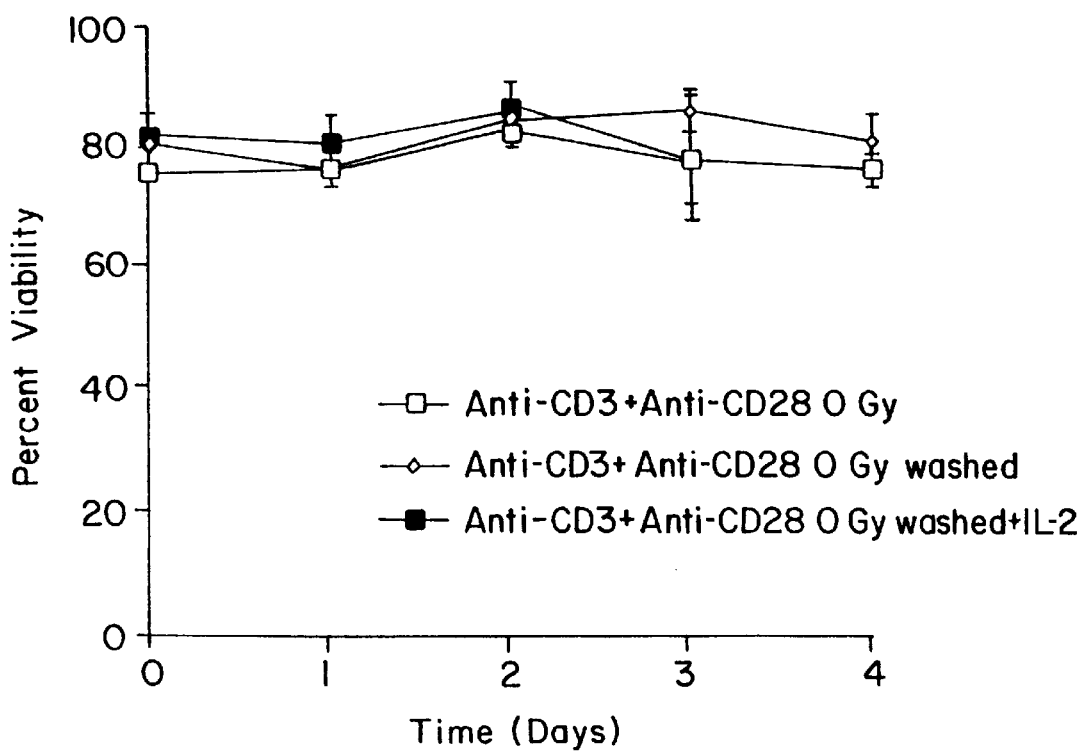
Figure 2D:
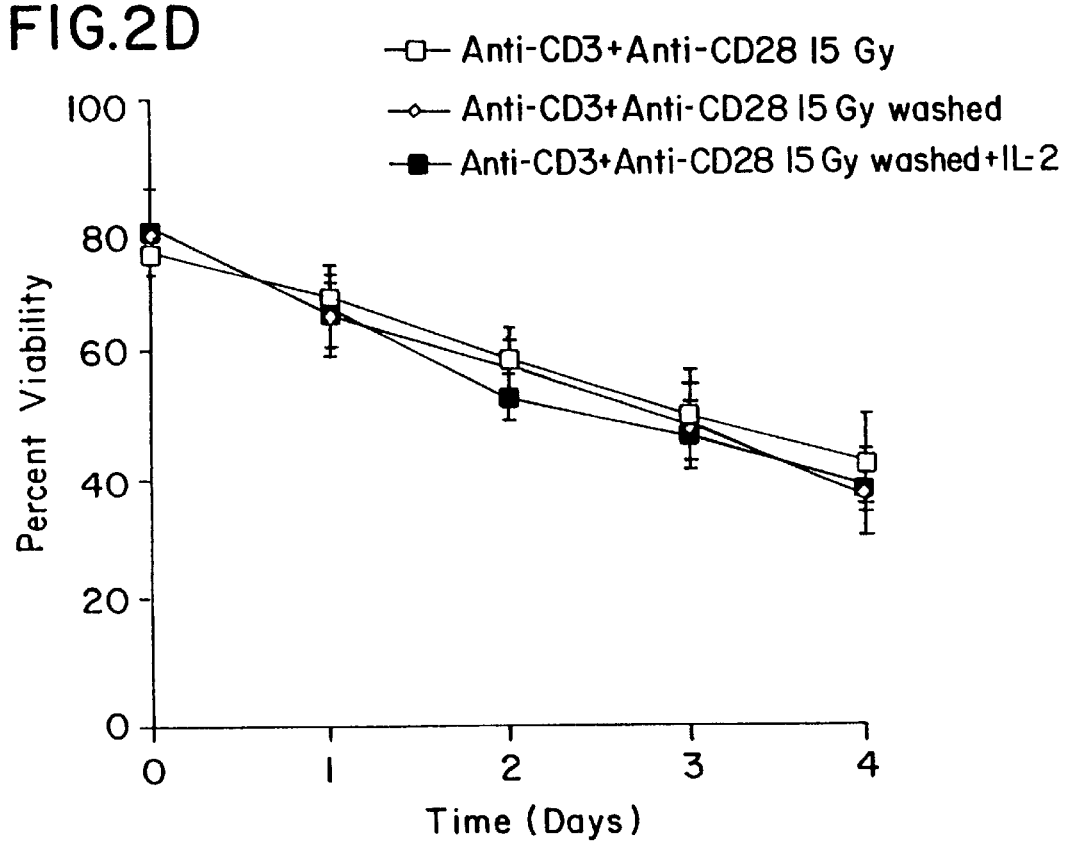
Figure 3A:
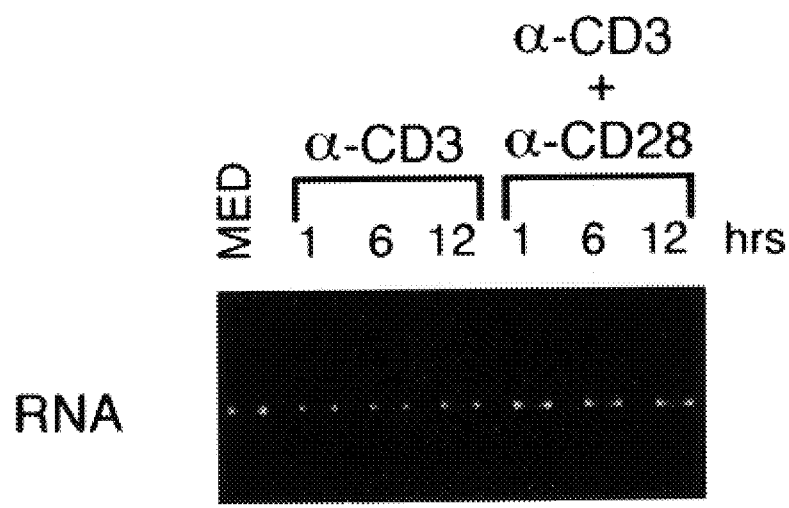
FIG. 3A–D: panels B, C, and D represent Northern blots showing the level of bcl-X, bcl-2 and HLA, respectively, expression in T cells incubated in medium alone (MED), incubated for 1, 6, or 12 hours in the presence of anti-CD3 antibody (αCD3), or incubated for 1, 6, or 12 hours in the presence of anti-CD3 and anti-CD28 (αCD3+αCD28). Panel A shows ethidium bromide staining of an aliquot of each RNA sample following electrophoresis on a non-denaturing agarose gel.
Figure 3B:
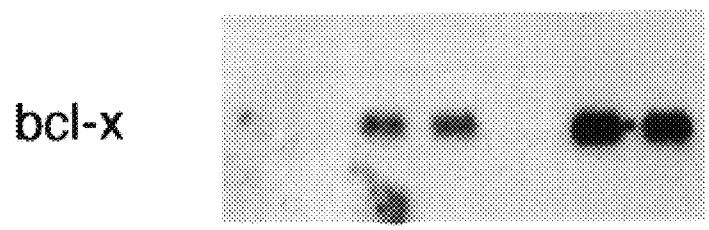
Figure 3C:
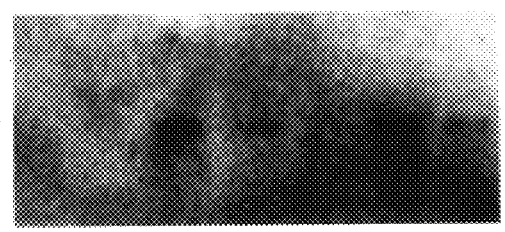
Figure 3D:
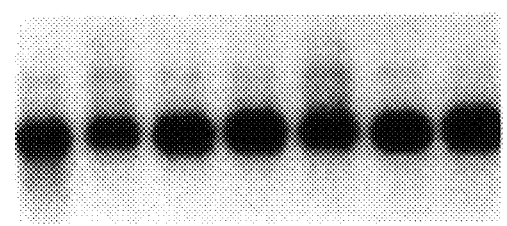
Figure 3E:
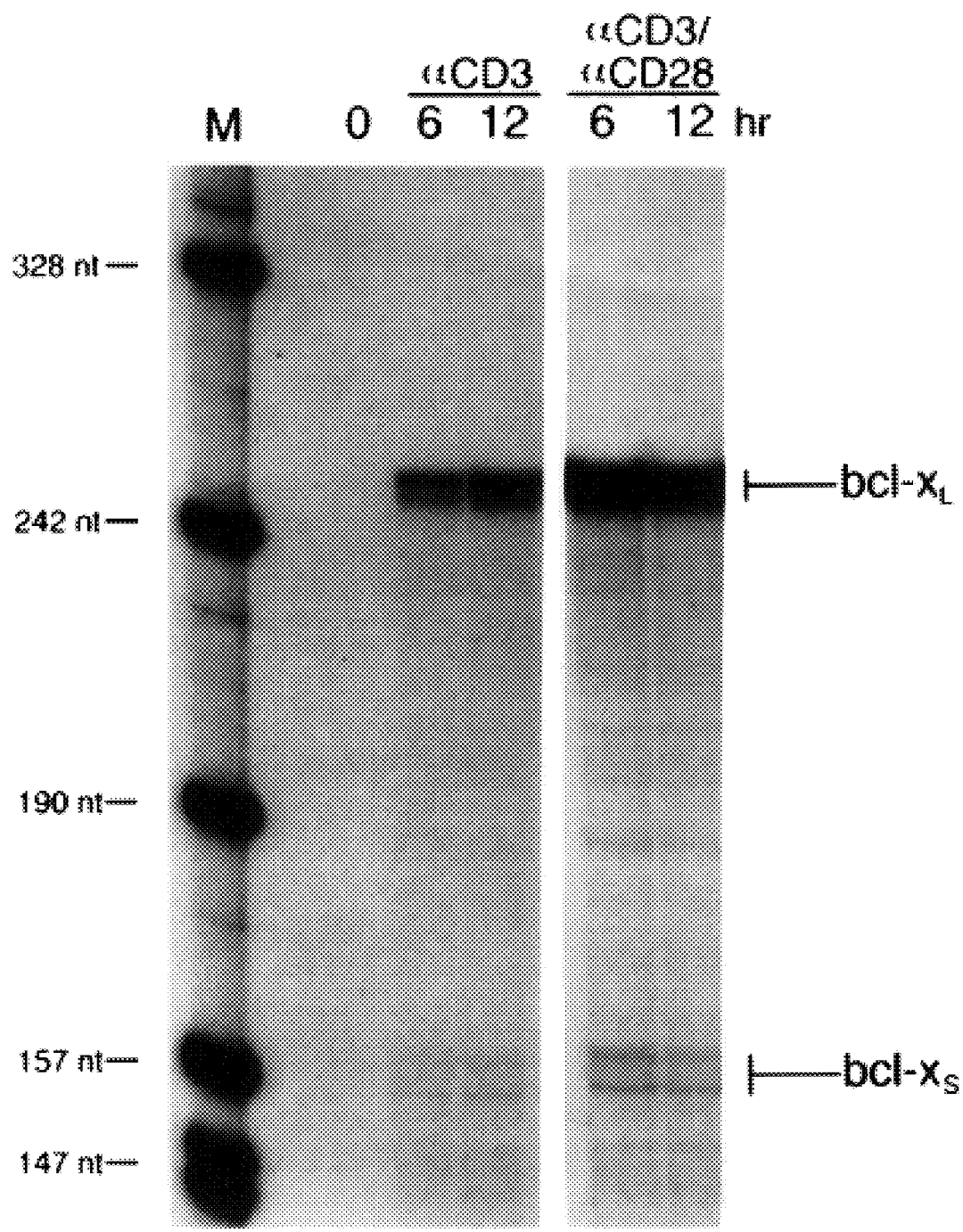
FIG. 3E is a photograph of a Western blot showing the amount of bcl-$X_L$ and Bcl-$X_S$ protein in T cells incubated alone (o) or with anti-CD3 (αCD3) for 6 or 12 hours or with anti-CD3 and anti-CD28 (αCD3+αCD28) for 6 or 12 hours.

The present invention provides methods for modulating T cell survival. In a preferred embodiment, the T cell is protected from cell death. The methods of the invention for protecting a T cell from cell death comprise contacting the T cell with at least one agent which augments bcl-$X_L$ protein level, such that survival of the T cell is enhanced. In one embodiment of this method, the agent which augments bcl-$X_L$ protein level is a nucleic acid encoding a bcl-$X_L$ protein, which is expressed upon introduction into the T cell. In yet another embodiment of this method, bcl-$X_L$ protein levels are augmented in a T cell by contacting the T cell with at least one agent which augments bcl-$X_L$ protein production, e.g. from the endogenous bcl-$X_L$ gene. In one embodiment, the at least one agent which augments bcl-$X_L$ protein level comprises an agent which interacts with a molecule on the surface of a T cell, such as CD28. The T cell may further be contacted with an agent which provides a primary activation signal to the T cell. In another embodiment, the at least one agent is an agent which acts intracellulary to augment bcl-$X_L$ protein level. In another embodiment, the invention further pertains to methods for rendering a T cell susceptible to cell death by reducing the level of bcl-$X_L$ protein in the T cell. T cells in which the level of bcl-$X_L$ protein is modulated according to the method of the invention can be T cells present in a subject or T cells cultured ex vivo. The methods of the invention are useful for modulating immune responses, i.e., boosting or repressing immune responses. Thus, the methods of the invention have numerous applications, such as stimulating an immune reaction (for example to fight an infection) or stimulating survival of T cells whose life span is reduced (for example as a result of an infection, such as an infection with a human immunodeficiency virus).

It has previously been observed that bcl-$X_L$ is capable of protecting the murine IL-3 dependent prolymphocytic cell line FL5.12 from IL-3 deprivation induced apoptosis (Boise, H. B. et al. (1993) *Cell* 74, 597 and PCT Patent Application WO 95/00642). Since apoptosis is an important mechanism regulating negative and positive selection of T cells during ontogeny, the authors analyzed the level of bcl-$X_L$ mRNA in T cells. Neither thymocytes, nor resting T cells, nor T cells activated with PMA and ionomycin contained any bcl-$X_L$ mRNA. However, thymocytes and activated T cells contained bcl-$X_S$ mRNA, an alternative splice form of the bcl-X gene which encodes a protein, bcl-$X_S$, shown to favor apoptosis (Boise, H. B. et al, supra, and PCT Patent Application WO 95/00642). Thus, these results suggested that control of apoptosis induced cell death during T cell ontogeny is mediated at least in part by control of the bcl-$X_S$ protein levels, rather than by control of bcl-$X_L$ protein levels.

The present invention is based, at least in part, on the discovery that transfection of T cells with a nucleic acid encoding human bcl-$X_L$ protein such that the bcl-$X_L$ protein level is increased in the T cell results in protection of the T cell from cell death. T cells modified in this manner were protected from cell death induced by different stimuli, such as γ-irradiation, T cell receptor crosslinking, Fas crosslinking, and growth factor deprivation. Thus, it is an object of the invention to modulate protein levels of bcl-$X_L$ in a T cell by contacting the T cell with an agent which modulates bcl-$X_L$ protein levels in the T cells, such that the T cells are protected from cell death or alternatively, rendered more susceptible to cell death. The methods of the invention are useful therapeutically in conditions in which it is desirable to prolong the survival of at least some of the T cells of a subject, such as T cells involved in fighting an infection. Alternatively, the methods of the invention are useful therapeutically in situations in which T cell death is desired, such as in autoimmune diseases.

1. Methods for Protecting a T Cell from Cell Death

The method of the invention involves "protecting a T cell from cell death". The term "T cell" is art-recognized and is intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a CD4+T cell, CD8+T cell, CD4+CD8+T cell, CD4–CD8–T cell, or any other subset of T cells. The language "protecting a T cell from cell death" is intended to include inhibiting, or at least delaying, occurrence of cell death in a T cell. Cell death is intended to encompass cell death occurring by any mechanism. Cell death can be programmed cell death (PCD), also termed "apoptosis". Death of a T cell by apoptosis is characterized by features including condensation of nuclear heterochromatin, cell shrinkage, cytoplasmic condensation, and in a later stage of apoptosis, endonuclease mediated cleavage of the DNA of the T cell into discrete fragments. Upon electrophoretic analysis of the DNA of a cell in which apoptosis has occurred, a characteristic "ladder" of discrete DNA fragments is apparent.

The invention pertains to methods for protecting a T cell from cell death occurring naturally, or cell death resulting from an induced signal in the cell. For example, apoptosis usually results from induction of a specific signal in the T cell. Thus, the method of the invention provides for protection of a T cell from cell death resulting from crosslinking of the T cell receptor in the absence of a costimulatory signal. It is known in the art that crosslinking of the T cell receptor, either by a polyclonal activator, such as an anti-CD3 antibody, or alternatively by an antigen on an antigen presenting cell, in the absence of a costimulatory signal results (e.g., in the absence of a signal through CD28/CTLA4) in T cell anergy or T cell death.

The method of the invention also allows for protecting a T cell from cell death resulting from growth factor depletion. For example, T cells typically require IL-2 for proliferation and the absence of IL-2 will result in cell death. Thus, increasing the level of bcl-$X_L$ protein in the T cell according to the methods of the invention will protect a normally IL-2 dependent T cell from cell death in the absence of IL-2 (i.e., the invention provides T cells that can survive in the absence of IL-2). Also within the scope of the invention are methods for protecting T cells from cell death resulting from the absence of other growth factors, cytokines, or lymphokines normally necessary for T cell survival. Examples of such factors include interleukins, colony stimulating factors, and interferons.

The method of the invention further allows for protecting a T cell from cell death that result from Fas or Tumor Necrosis Factor Receptor (TNFR) crosslinking. It has been shown that crosslinking of the Fas receptor on a T cell results in apoptotic cell death of the T cell. The Fas and TNFR proteins share considerable homology and it is possible that they belong to an extended family of proteins inducing cell death upon crosslinking. Thus, the method of the invention likely is useful for protecting T cells from cell death resulting from crosslinking of any receptor belonging to that family.

The method of the invention also provides a means for protecting T cells from cell death induced by exposure to certain hormones, such as glucocorticoids, for example dexamethasone. Moreover, cell death can also occur as a result of stress which is known to induce elevated glucocorticoid levels in a subject. Thus, the method of the invention also provides protection against T cell death resulting from exposure of a subject to stress.

Furthermore, the method of the invention allows for protecting T cells from cell death induced by DNA-damaging agents.

T cells also undergo cell death during T cell ontogeny. The processes of proliferation and differentiation of T cells is tightly regulated and includes positive as well as negative selection of T cells. Methods for influencing T cell survival during this process are also within the scope of the invention.

T cell death can also result from activity in the T cell of a protein inducing apoptosis, such as bcl-$X_S$, Bad, p53, c-myc, or Interleukin-1β converting enzyme (ICE)(Savill, J. (1994) *Eur. J. Clin. Investigat.* 24, 715). Thus, methods within the scope of the invention include methods protecting against cell death associated with these proteins.

1.2. Methods for Protecting a T Cell from Cell Death Comprising Introducing a Nucleic Acid Encoding a bcl-$X_L$ Protein into the T Cell In one embodiment of the invention, a T cell is protected from cell death by introducing into the cell a nucleic acid encoding a bcl-$X_L$ protein, such that bcl-$X_L$ protein level in the T cell is augmented. The nucleic acid molecule encoding a bcl-$X_L$ protein is in a form that allows expression of the gene in the T cell, such that bcl-$X_L$ protein is produced in the cell.

1.2.1. Nucleic Acids Encoding bcl-$X_L$ Protein or Modified Forms Thereof

The language "nucleic acid molecule encoding bcl-$X_L$" is intended to include any nucleic acid molecule that will be transcribed and translated into a bcl-$X_L$ protein upon introduction of the nucleic acid molecule into a T cell (e.g., the molecule can further contain appropriate control elements for regulating expression of bcl-$X_L$). The nucleic acid molecule encoding bcl-$X_L$ can consist of only the coding region of the corresponding bcl-$X_L$ gene, or alternatively it can contain noncoding regions, such as 5' or 3' untranslated regions, introns, fragments thereof, or other sequences.

The bcl-$X_L$ protein is encoded by the bcl-X gene. As a result of differential splicing, the bcl-X gene produces 2 different mRNA molecules, one of which encodes bcl-$X_L$ (for long form of bcl-X) protein and the other which encodes the smaller protein bcl-$X_S$ (for short form of bcl-X). The bcl-$X_S$ differs from the bcl-$X_L$ protein by lacking a stretch of 63 amino acids. This deletion results from splicing of the second coding exon present in bcl-$X_L$ to a more proximal 5' splice donor within the first coding exon. Thus, it is preferable to use the bcl-$X_L$ cDNA for expression of bcl-$X_L$ in T cells, rather than a genomic fragment containing the bcl-X gene, which may result in production of both bcl-$X_L$ and bcl-$X_S$ proteins.

For treating human cells, the nucleic acid encoding bcl-$X_L$ is preferably of human origin although nucleic acids from other animal species are also encompassed by the invention. Moreover, bcl-$X_L$ nucleic acids can be used across species as long as the protein encoded by the nucleic acid protects T cells from cell death upon introduction of the nucleic acid into the T cell. In a preferred embodiment of the invention, the nucleic acid encoding bcl-$X_L$ protein is the human cDNA (SEQ ID NO: 1). Nucleic acids encoding bcl-$X_L$ protein which are within the scope of the invention are disclosed in the Published PCT application WO 95/00642, and in the following references: Boise et al. (1993) *Cell* 74, 597; and Fang et al. (1994) *J. Immunol.* 153, 4388. Moreover, the nucleotide sequence of human bcl-$X_L$ cDNA, and amino acid sequence of human bcl-$X_L$ protein are shown in SEQ ID NO: 1 and 2, respectively. The nucleic acid molecule can encode the full length bcl-$X_L$ protein or alternatively the nucleic acid can encode a peptidic fragment of bcl-$X_L$ that is sufficient to confer protection from cell death on a T cell when introduced into the T cell. The nucleic acid can encode the natural bcl-$X_L$ or fragment thereof, or a modified form of the bcl-$X_L$ protein or fragment thereof. Modified forms of the natural bcl-$X_L$ protein which are within the scope of the invention are described below.

The method of the invention is intended to include the use of fragments, mutants, or variants (e.g., modified forms) of bcl-$X_L$ protein that retain the ability to protect T cells from cell death. A "form of bcl-$X_L$ protein" is intended to mean a protein that shares a significant homology with the natural bcl-$X_L$ protein and is capable of protecting a T cell from cell death. A "form of bcl-$X_L$ protein" is not intended to include the protein Bcl-2. The terms "biologically active bcl-$X_L$ protein" or "biologically active form of a bcl-$X_L$ protein" or functionally active form of bcl-$X_L$ protein", as used herein, are meant to include forms of bcl-$X_L$ proteins that are capable of protecting a T cell from cell death. One skilled in the art can select such forms of bcl-$X_L$ protein based on their ability to protect T cells from cell death upon introduction of a nucleic acid encoding the bcl-$X_L$ protein in the T cell. The ability of a specific form of bcl-$X_L$ to protect T cells from cell death can be determined, for example by transfecting a nucleic acid encoding the specific form of bcl-$X_L$ into a T cell, such that the bcl-$X_L$ protein is synthesized in the T cells under conditions where cell death normally is induced in the T cell. The form of bcl-$X_L$ protein has a protective effect against cell death in T cells if less cell death occurs in a population of T cells modified to express a form of bcl-$X_L$ than in a population of T cells that has not been modified to express a form of bcl-$X_L$ upon induction of cell death. Cell death can be monitored by various means. Extent of cell death in a population of cells can be determined for example by counting the number of T cells in both populations using a haemocytometer or a Coulter Counter. A preferred method for determining the extent of cell death in a population of T cells is by propidium iodide exclusion assays. Propidium iodide exclusion assays can be carried out by incubating the T cells with propidium iodide, a dye which is absorbed predominantly by dead cells and is excluded from live cells. The extent of cell death is then determined by Fluorescence Activated Cell Sorter (FACS) analysis, as described in Example 6 of the present application. Additional dyes that can be used include acridine orange and Hoechst 33342. Other methods for measuring the extent of cell death in a population of T cells include various methods of end-labelling of cleaved DNA (Gavrieli, Y. et al. (1992) *J. Cell Biol.* 119, 493). Another method for determining the extent of cell death in a population of T cells includes electrophoretic analysis of the nucleic acid of the T cells. In this method, the nucleic acid of the T cells which can be in a purified or unpurified form is subjected to gel electrophoresis followed by staining of the gel with ethidium bromide and visualization of the nucleic acid under ultraviolet light. The nucleic acid from a population of T cells in which at least some of the T cells have gone under apoptosis will have the appearance of a "ladder", i.e., a population of discrete fragments of DNA. In contrast, DNA of T cells that have not undergone apoptosis will appear as a single high molecular weight band.

Several assays can be used for testing a form of bcl-$X_L$ protein for its ability to protect a T cell from cell death. These assays include assays in which a population of T cells is induced to undergo apoptosis by contacting the population of T cells with specific agents. Such agents include agents that crosslink the T cell receptor, such as an anti-CD3 antibody, agents that crosslink Fas or the TNF receptor, and glucocorticoids. Alternatively, cell death can be induced in T cells by growth factor deprivation, such as IL-2 deprivation. These assays are described throughout the specification, in particular in Examples 6 and 7.

Production of fragments of bcl-$X_L$ in the T cell can be obtained by introducing into the T cell a fragment of the nucleic acid encoding the bcl-$X_L$ protein fragment. The nucleic acid can be a cDNA or alternatively it can be a genomic DNA fragment. Mutants of bcl-$X_L$ can be prepared, for example, by introducing nucleotide base pair modifications (e.g., substitutions, deletions, additions) to a nucleic acid molecule encoding the bcl-$X_L$ protein (e.g., a bcl-$X_L$ cDNA) by standard methods, such as site-directed mutagenesis or polymerase chain reaction-mediated mutagenesis. Preferred modifications of bcl-$X_L$ included those that modify the half-life of the bcl-$X_L$ protein in the T cell. Thus, in specific embodiments it may be desirable to introduce into the T cell a form of bcl-$X_L$ protein which has a very short half-life, whereas in other embodiments of the method, it may be desirable to introduce into the T cell a form of bcl-$X_L$ which has a long half-life.

In a preferred embodiment, the bcl-$X_L$ protein is modified to facilitate interaction with the "Bax" protein and to inhibit, or reduce interaction with the "Bad" protein. It has been demonstrated that the protective effect of bcl-$X_L$ against apoptosis in cells may be mediated through a heterodimer composed of one bcl-$X_L$ protein and another protein termed "Bax". However, further data indicate that a protein termed "Bad" also may interact with bcl-$X_L$ and that a heterodimer composed of bcl-$X_L$ and Bad may inactivate the protective effect of bcl-$X_L$ against cell death (Yang, E. et al. (1995) *Cell* 80, 285). Moreover, it has also been shown that Bad is capable of displacing the Bax protein from the Bax/bcl-$X_L$ heterodimer to form a bcl-$X_L$/Bad heterodimer. Thus, in a preferred embodiment of the method, a T cell is protected from cell death by introducing into the T cell a nucleic acid encoding a bcl-$X_L$ protein that is modified such that binding of the modified form of bcl-$X_L$ to Bad is inhibited, or at least reduced, whereas binding of the modified form of bcl-$X_L$ to Bax is not significantly affected as compared to wildtype bcl-$X_L$ protein. In a preferred embodiment of the invention, the modification of bcl-$X_L$ protein includes substituting at least one amino acid of bcl-$X_L$ that is located in the Bcl-2 homology (BH) domains 1 or 2 ("BH1" and "BH2", respectively). BH1 is located between amino acids 129 and 148 of the human bcl-$X_L$ protein (SEQ ID NO: 2) and BH2 is located between amino acids 180 and 191 of the human bcl-$X_L$ protein (SEQ ID NO: 2) (Yang, E. et al. (1995) *Cell* 80, 285).

Furthermore, it will be appreciated by those skilled in the art that changes in the primary amino acid sequence of bcl-$X_L$ are likely to be tolerated without significantly impairing the ability of the bcl-$X_L$ molecule to protect T cells form cell death. Accordingly, mutant forms of bcl-$X_L$ that have amino acid substitutions, deletions and/or additions as compared to the naturally occurring amino acid sequence of a bcl-$X_L$ molecule yet still retain the functional activity of the natural form of bcl-$X_L$ as described herein are also encompassed by the invention. To retain the functional properties bcl-$X_L$, preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

1.2.2. Regulatory Sequences for Expression of bcl-$X_L$ Encoding Nucleic Acid in T Cells To express a nucleic acid molecule encoding bcl-$X_L$ in a T cell such that the level of bcl-$X_L$ protein is increased in the T cell (to thereby protect the T cell is from cell death) the nucleic acid must be operably linked to regulatory elements. "Operably linked" is intended to mean that the nucleotide sequence encoding bcl-$X_L$ is linked to at least one regulatory sequence in a manner which allows expression of the nucleotide sequence in the T cell. Regulatory sequences are selected to direct expression of the desired protein in an appropriate T cell. Accordingly, the term "regulatory sequence" includes promoters, enhancers and other expression control elements. Such regulatory sequences are known to those skilled in the art and are further described in Goeddel, *Gene Expression Technology: Methods in Enzymology* 185, Academic Press, San Diego, Calif. (1990).

These regulatory elements include those required for transcription and translation of the nucleic acid encoding bcl-$X_L$, and may include promoters, enhancers, polyadenylation signals, and sequences necessary for transport of the molecule to the appropriate cellular compartment, which is preferably the outer mitochondrial membrane (Gonzales-Garcia, M. et al. (1994) *Development* 120, 3033). When the nucleic acid is a cDNA in a recombinant expression vector, the regulatory functions responsible for transcription and/or translation of the cDNA are often provided by viral sequences. Examples of commonly used viral promoters include those derived from polyoma, Adenovirus 2, cytomegalovirus and Simian Virus 40, and retroviral LTRs.

Regulatory sequences linked to the cDNA can be selected to provide constitutive or inducible transcription. Inducible transcription can be accomplished by, for example, use of an inducible enhancer. Thus, in a specific embodiment of the invention the nucleic acid molecule encoding a form of bcl-$X_L$ is under the control of an inducible control element such that expression of the form of bcl-$X_L$ can be turned on or off (or intermediate levels in between) using an agent which affects the inducible control element (e.g., expression can be modulated by modulating the concentration of the inducing agent in the presence of the T cell). This allows for switching on or off the protective effect of bcl-$X_L$ against cell death in the T cells. It may indeed be desirable to promote T cell survival only in certain conditions or only for a certain amount of time. For example, at the site of an infection in a subject, it may be desirable to boost the immune reaction to eliminate the infectious agent in a limited time frame. However, upon clearance of the infectious agent it may be desirable to eliminate the T cells. Thus, the expression of bcl-$X_L$ in the T cells located at the site of an infection can be stimulated through the inducible control element by contacting the T cells with the inducing agent. Then, upon clearance of the infection, inducing agent can be removed to stop production of bcl-$X_L$ protein in the T cells.

Inducible regulatory systems for use in mammalian cells are known in the art, for example systems in which gene expression is regulated by heavy metal ions (Mayo et al. (1982) *Cell* 29:99–108; Brinster et al. (1982) *Nature* 296:39–42; Searle et al. (1985) *Mol. Cell. Biol.* 5: 1480–1489), heat shock (Nouer et al. (1991) in *Heat Shock Response*, e.d. Nouer, L. , CRC, Boca Raton, Fla., pp167–220), hormones (Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604) or tetracycline (Gossen, M. and Bujard, H. (1992) *Proc. Natl. Acad Sci. USA* 89:5547–5551). Other systems providing inducible gene expression which is controllable by contacting the T cells with specific inducing agents are described in the Published PCT Application No. WO 94/18317 and published PCT Application No. WO 93/23431.

Inducible control elements may function in all T cells, or alternatively, only in a specific subset of T cells, such as in CD4+T cells, CD8+T cells, T helper 1 (Th1), T helper 2 (Th2) cells. Inducible control elements can also be selected which are regulated by one agent in one type of T cells (such as CD4+T cells) yet which are regulated by another agent in another type of T cells (such as CD8+T cells).

In another embodiment of the invention, the nucleic acid molecule which encodes a bcl-$X_L$ protein is under the control of regulatory sequences which constitutively drive the expression of the nucleic acid molecule. In a specific embodiment of the invention, T cells from a subject infected with HIV are modified to constitutively express a bcl-$X_L$ protein, such that the T cells of the subject are constitutively protected from cell death. Regulatory elements which drive constitutive expression of nucleic acid molecules to which they are operably linked are preferably viral promoters. Examples of commonly used viral promoters include those derived from polyoma, Adenovirus 2, cytomegalovirus and Simian Virus 40, and retroviral LTRs. Alternatively, T cell-specific enhancers can be used, e.g. T cell receptor enhancers (see e.g. Winoto and Baltimore (1989) EMBO J. 8:729–733).

The nucleic acid molecule encoding a bcl-$X_L$ protein operably linked to regulatory elements is typically carried in a vector. Examples of vectors include plasmids, viruses or other nucleic acid molecules comprising, for example, sequences that are necessary for selection and amplification of the nucleic acid molecule in bacteria. Thus, a nucleic acid molecule comprising a nucleotide sequence encoding a bcl-$X_L$ protein operably linked to regulatory control elements, is also referred to herein as "bcl-$X_L$ expression vector". Vectors, e.g. viral vectors, are further discussed below.

1.2.3. Methods for Introducing a Nucleic Acid Molecule Encoding a bcl-$X_L$ Protein into a T Cell The nucleic acid molecule encoding a bcl-$X_L$ protein can be introduced into the T cell by various methods typically referred to as transfection. The terms "transfection" or "transfected with" refers to the introduction of exogenous nucleic acid into a mammalian cell and are intended to encompass a variety of techniques useful for introduction of nucleic acids into mammalian cells, including electroporation, calcium-phosphate precipitation, DEAE-dextran treatment, lipofection, microinjection, and viral infection. Suitable methods for transfecting mammalian cells can be found in Sambrook et al. (*Molecular Cloning: A Laboratory Manual.* 2nd Edition. Cold Spring Harbor Laboratory press (1989)) and other laboratory textbooks.

In a preferred embodiment of the invention, the nucleic acid molecule encoding a bcl-$X_L$ protein is introduced into a T cell by using a viral vector. Such viral vectors include, for example, recombinant retroviruses, adenovirus, adeno-associated virus, and herpes simplex virus-1. Retrovirus vectors and adeno-associated virus vectors are generally considered to be the recombinant gene delivery system of choice for the transfer of exogenous genes in vivo, particularly into humans. Alternatively, such vectors can also be used for introducing exogenous genes ex vivo into T cells. These vectors provide efficient delivery of genes into T cells, and the transferred nucleic acids are stably integrated into the chromosomal DNA of the host cell. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A.D. (1990) *Blood* 76:271). Thus, recombinant retrovirus can be constructed in which part of the retroviral coding sequence (gag, pol, env) has been replaced by nucleic acid encoding a bcl-$X_L$ protein of the invention rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology,* Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm.

Furthermore, it has been shown that it is possible to limit the infection spectrum of retroviruses, and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). Thus, in a specific embodiment of the invention, viral particles containing a nucleic acid molecule encoding a form of bcl-$X_L$, are modified, for example, according to the methods described above, such that they can specifically target subsets of T cells. For example, the viral particle can be coated with antibodies to surface molecule that are specific to certain types of T cells. In particular, it is possible to selectively target CD4+T cells by linking to the viral particle antibodies that recognize the CD4 molecule on the T cell. Thus, infection of CD4+T cells will occur preferentially over infection of CD8+T cells. This method is particularly useful when protection of only specific subsets of T cells against cell death is desired. Moreover, in specific embodiments in which the method of the invention is used in vivo, it may be desirable to limit the introduction of the nucleic acid molecule encoding a bcl-$X_L$ protein to T cells or specific subsets.

Additional retroviral systems for introducing and expressing a nucleic acid molecule encoding a bcl-$X_L$ protein in T cells including primary T cells are described in Kasid, A. et al. (1990) *Proc. Natl. Acad. Sci. U.S.A.* 87, 473; Morecki, S. et al. (1991) *Cancer Immunol. Immunother.* 32, 342; Culver, K. et al. (1991) *Proc. Natl. Acad. Sci U.S.A.* 88, 3155; and Finer, M. H. et al. (1994) *Blood,* 83, 43.

Another viral gene delivery system useful in the present invention utilitizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use, and therefore favored by the present invention, are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted nucleic acid molecule encoding a bcl-$X_L$ protein can be under control of, for example, the E1A promoter, the major late promoter (MLP) and associated leader sequences, the E3 promoter, or exogenously added promoter sequences.

Yet another viral vector system useful for in vivo delivery of a nucleic acid molecule encoding a bcl-$X_L$ protein is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as few as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790). Other viral vector systems that may have application in gene therapy have been derived from herpes virus, vaccinia virus, and several RNA viruses.

In addition to carrying a bcl-$X_L$-encoding sequence, an expression vector may also contain a gene encoding a selectable marker. Preferred selectable markers include those which confer resistance to drugs such as G418, hygromycin and methotrexate. Selectable markers may be introduced on the same vector (e.g. plasmid) as the nucleic acid molecule encoding a bcl-$X_L$ protein or may be introduced on a separate vector (e.g. plasmid).

Alternatively, the nucleic acid molecule encoding a bcl-$X_L$ protein can be carried by and delivered into a cell by a cell-delivery vehicle. Such vehicles include, for example, cationic liposomes (lipofectin) or derivatized (e.g. antibody conjugated) polylysine conjugates, gramicidin S, artificial viral envelopes. These vehicles can deliver a nucleic acid encoding a bcl-$X_L$ protein that is carried by vector e.g. a plasmid or virus DNA. In a specific embodiment, efficient gene expression in primary T lymphocytes, in particular in CD3+, CD4+ and CD8+T cells, is obtained using adeno-associated virus plasmid DNA complexed to cationic liposomes, as described in Philip, R. et al. (1994) *Mol. Cell. Biol.* 14, 2411.

In another embodiment of the invention, the nucleic acid molecule encoding a bcl-$X_L$ protein is delivered into a specific cell in the form of a soluble molecular complex. The complex contains the nucleic acid releasably bound to a carrier comprised of a nucleic acid binding agent and a cell-specific binding agent which binds to a surface molecule of the specific cell and is of a size that can be subsequently internalized by the cell. Such complexes are described in U.S. Pat. No. 5,166,320.

In another embodiment of the invention the nucleic acid encoding a bcl-$X_L$ protein is introduced into T cells by particle bombardment, as described in Yang, N.-S. and Sun, W. H. (1995) *Nature Medicine* 1, 481.

1.1. Methods Employing Agents which Augment bcl-$X_L$ Protein Level

In one embodiment, the method of the invention involves enhancing the survival of a T cell by contacting the T cell with at least one agent which increases bcl-XL protein level in the T cell. In a preferred embodiment of the invention, the at least one agent which interacts with the T cell to increase the level of bcl-$X_L$ protein level includes one or more agents which interact with molecules on the surface of the T cell, such as the T cell receptor and CD28. In another embodiment of the invention, the at least one agents which augments bcl-$X_L$ protein level in the T cell is an agent which acts intracellularly, for example by increasing expression of the bcl-X gene. The language "an agent which acts intracellularly to augment bcl-$X_L$ protein level in the T cell" is intended to include agents which do not bind to a surface receptor on the T cell, but rather mimic or induce an intracellular signal (e.g., second messenger) transduced from crosslinking a receptor on the T cell which results in augmentation of bcl-$X_L$ protein level in the T cell. The agent may stimulate the production of bcl-$X_L$ protein in the T cell through various mechanisms, such as by increasing transcription of the bcl-$X_L$ gene, stabilizing bcl-$X_L$ mRNA, or by increasing translation of bcl-$X_L$ mRNA. In a preferred embodiment, bcl-$X_L$ protein level is augmented selectively, i.e., without concomitant augmentation of Bcl-$X_S$ protein level.

The language "stimulate expression of the endogenous gene" is intended to include effecting the bcl-X gene in a cell, such that the level of the bcl-$X_L$ protein encoded by the gene is increased in the cell. The language "stimulate the transcription" is intended to include effecting transcription such that the amount of mRNA transcribed is increased. The term "endogenous bcl-X gene" is intended to mean the bcl-X gene which is naturally in the T cell, as opposed to an "exogenous bcl-X gene" which has been introduced into the T cell.

In a preferred embodiment of the invention, a T cell is contacted with at at least one agent, resulting in augmentation of bcl-$X_L$ protein level in the T cell and protection of the T cell against cell death. In a preferred embodiment, survival of a T cell is enhanced by contacting the T cell with a combination of agents which stimulate the T cell. A preferred combination of agents is a combination of agents which comprise agents activating the T cell and providing a costimulatory molecule to the T cell. For example, T cell survival can be enhanced by contacting the T cell with a first agent which provides a primary activating signal to the T cell and a second agent which provides a costimulatory signal to the T cell. A much preferred combination includes an agent that stimulates the T cell receptor and an agent which provides a costimulatory signal to the T cell, such that bcl-$X_L$ protein level is increased in the T cell.

The language "primary activation signal" is intended to include signals, typically triggered through the T cell receptor (TCR)/CD3 complex, that induce activation of T cells. Activation of a T cell is intended to include modifications of a T cell, such that the T cell is induced to proliferate and differentiate upon receiving a second signal, such as a costimulatory signal. In a specific embodiment, the primary activation signal is provided by an agent which contacts the T cell receptor or the CD3 complex associated with the T cell receptor. In a preferred embodiment, the agent is an antibody reactive against CD3, such as the monoclonal antibody OKT3 (available from the American Type Culture Collection, Rockville, Md.; No. CRL 8001). In another embodiment of the invention, the stimulating agent is an agent that stimulates the CD2 complex on T cells, such as a combination of antibodies, e.g. T11.3+T11.1 or T11.3+ T11.2 (see e.g., Meuer, S. C. et al. (1984) *Cell* 36:897–906). In yet another embodiment, the primary activating signal is provided by an antigen on an antigen presenting cell. Thus, it is possible to selectively stimulate survival of specific T cell clones in a population of T cells by contacting the T cells with one or more antigens on one or more antigen presenting cells, and optionally a second agent which provides a costimulatory signal.

In a preferred embodiment of the invention, the T cells are stimulated with a combination of agents that stimulate both a primary activation signal and a costimulatory signal in the T cell. The term "costimulatory agent" is intended to include agents which provide a costimulatory signal in T cells, such that a T cell that has received a primary activation signal (e.g. an activated T cell) is stimulated to proliferate or to secrete cytokines, such as IL-2, IL-4, or interferon-γ. In a specific embodiment, the costimulatory agent interacts with CD28 or CTLA4 molecules on the surface of the T cells. In an even more specific embodiment, the costimulatory signal is a ligand of CD28 or CTLA4, such as a B-lymphocyte antigen B7-1 or B7-2. The language "stimulatory form of a natural ligand of CD28" is intended to include B7-1 and B7-2 molecules, fragments thereof, or modifications thereof, which are capable of providing costimulatory signals to the T cells. Stimulatory forms of natural ligands of CD28 can be identified by, for example, contacting activated T cells with a form of a natural ligand of CD28 and performing a standard T cell proliferation assay. Thus, a stimulatory form of a natural ligand of CD28 is capable of stimulating proliferation of the T cells. Stimulatory forms of natural ligands of CD28/CTLA4 are described, for example, in PCT Publication No. WO 95/03408.

Other agents that can be used to protect T cells from cell death include agents that stimulate one or more intracellular signal transduction pathways involved in T cell activation and/or costimulation, such that bcl-$X_L$ protein level is increased in the T cell. In a preferred embodiment of the invention, the stimulatory agent is a calcium ionophore, such as ionomycin or A23187. Alternatively, the stimulatory agent can be an agent which stimulates protein kinase C, such as a phorbol ester. A preferred phorbol ester is phorbol-12,13-dibutyrate. In an even more preferred embodiment of the invention, T cells are contacted with a combination of a calcium ionophore and a phorbol ester. The stimulatory agent can also be an agent which activates protein tyrosine kinases. A preferred agent that stimulates protein tyrosine kinases is pervanadate (O'Shea, J. J., et al. (1992) *Proc. Natl. Acad. Sci. USA* 89:10306).

Other agents which can be employed to stimulate T cell survival include agents such as polyclonal activators that are capable of augmenting bcl-$X_L$ protein level. Polyclonal activators include agents that bind to glycoproteins expressed on the plasma membrane of T cells and include lectins, such as phytohemaglutinin (PHA), concanavalin (Con A) and pokeweed mitogen (PWM).

Superantigens capable of augmenting bcl-$X_L$ protein level in T cells are also within the scope of the invention. The term "super-antigen" as defined herein is intended to include bacterial enterotoxins, or other bacterial proteins capable of stimulating proliferation of T cells. Super-antigens include staphylococcal enterotoxins (SE), such as SEA, SEB, SEC, SED, and SEE. Super-antigens can also be of viral origin, such as retroviral super-antigens.

Yet other agents that may be used to stimulate T cell survival include lymphokines, which alone or in combination with another agent to increase bcl-$X_L$ protein level in the T cell. Thus, in a preferred embodiment of the invention, T cells are contacted with a combination of an agent which provides a primary activation signal to the T cells (e.g., an anti-CD3 antibody) and an effective amount of IL-2 such that bcl-$X_L$ protein level is increased in the T cell.

Additional agents that are capable of preventing T cell death by augmenting bcl-$X_L$ protein level, either alone or in combination with other agents, may be identified by contacting the T cells with the agent alone or together with another agent and monitoring bcl-$X_L$ protein level by, for example, Western blot analysis, as described herein.

The agents within the scope of the invention can be used in solution, or attached to a solid surface. The solid surface can be, for example, the surface of a tissue culture dish or a bead. Depending on the nature of the stimulatory agent, linkage to the solid surface can be performed by methods well known in the art. For example, proteins can be chemically crosslinked to the cell surface using commercially available crosslinking reagents (Pierce, Rockford Ill.) or immobilized on plastic by overnight incubation at 4° C. If several agents are used for augmenting bcl-$X_L$ levels in T cells, some agents may be in solution and some agents may be attached to a solid support. In a preferred embodiment, the T cells are contacted with a combination of solid phase coupled anti-CD3 antibody and soluble anti-CD28 antibody.

Agents which act intracellularly to augment bcl-$X_L$ protein level can be identified using standard assays for defection of bcl-$X_L$ protein levels in cells. For example T cells can be incubated in the presence or absence of a test agent and the amount of bcl-$X_L$ protein produced by the cell at different times can be determined by Western blot analysis, as described and in the Examples section in the published PCT Application Number WO 95/00642, incorporated herein by reference. Thus, preferred agents for practicing the method of the invention include those that induce a significant increase in bcl-$X_L$ protein level, as determined by Western blot analysis.

Additionally, agents that can be used to increase protein level of bcl-$X_L$ in T cells can be identified by analysis of the regulatory region of the bcl-X gene to identify. DNA sequences that regulate transcription of the gene by specific agents. For example, transcriptional activators that specifically bind to these sequences can be used to stimulate bd-X gene expression. It can then be confirmed by Western blot analysis that these agents increase bcl-$X_L$ protein levels in the cell.

In a specific embodiment of the invention, the agent acts selectively, or at least preferentially, on T cells to augment bcl-$X_L$ protein level. Thus, administration of the agent to a subject results in augmentation of bcl-$X_L$ protein level only in T cells, or at least preferably in T cells. T cell specific agents can be identified by contacting in vitro different types of cells with the agent and measuring the level of bcl-$X_L$ protein in the cells by Western blot analysis. Thus, preferred agents are those that lead to an increase in bcl-$X_L$ protein level only in T cells, or at least preferably in T cells.

In a preferred embodiment of the invention, the agent which acts intracellularly to augment bcl-$X_L$ protein level is an agent which has a relatively short half-life. Such an agent allows for a better control of the effects of the agent. In particular, such an agent may allow for a short, medium, or long stimulation of cell survival in the T cell. Indeed, in specific embodiments of the invention, it is preferable to increase T cell survival only transiently, for example in conditions where the agent is used to boost an immune reaction at the site of an infection. An immune reaction is controlled at least in part by controlling the half-life of the T cell. Absence of T cell death may, in certain conditions, eventually result in deleterious effects. However, in other embodiments of the invention, the agent which acts intracellularly to augment bcl-$X_L$ protein level has a long half-life, such that fewer administrations of the agent to the subject are required to obtain a longer protective effect against T cell death.

1.3. Methods for Protecting a T Cell from Dell death by Introducing a Protein in the T Cell In another embodiment of the invention, T cells are protected from cell death by a method comprising contacting the T cell with a bcl-$X_L$ protein in a form suitable for uptake by the T cell. Thus, in a specific embodiment of the invention, a bcl-$X_L$ protein is synthesized in vitro by conventional techniques, such as in a bacterial expression system, and delivered to the T cell in a suitable vehicle. Suitable vehicles include liposomes that can be modified to target specific cells, in particular T cells, or a selective subset of T cells.

bcl-$X_L$ protein can be produced in vitro by inserting a nucleic acid molecule encoding bcl-$X_L$ or a biologically active form of bcl-$X_L$ into various expression vectors, which in turn direct the synthesis of the corresponding protein in a variety of hosts, particularly eucaryotic cells, such as mammalian or insect cell culture but also procaryotic cells, such as E. coli. Expression vectors within the scope of the invention comprise a nucleic acid as described herein and a promoter operably linked to the nucleic acid. Such expression vectors can be used to transfect host cells to thereby produce the protein encoded by the nucleic acid as described herein. An expression vector of the invention, as described herein, typically includes nucleotide sequences encoding a bcl-$X_L$ protein operably linked to at least one regulatory sequence. Regulatory sequences have been described above. It should be understood that the design of the expression vector may depend on such factors as the choice of the host cell to be transfected and/or the type and/or amount of protein desired to be expressed.

An expression vector of the invention can be used to transfect cells, either procaryotic or eucaryotic (e.g., mammalian, insect or yeast cells) to thereby produce proteins encoded by nucleotide sequences of the vector. Expression in procaryotes is most often carried out in E. coli with vectors containing constitutive or inducible promoters. Certain E. coli expression vectors (so called fusion-vectors) are designed to add a number of amino acid residues to the expressed recombinant protein, usually to the amino terminus of the expressed protein. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Examples of fusion expression vectors include pGEX (Amrad Corp., Melbourne, Australia) and pMAL (New England Biolabs, Beverly, Mass.) which fuse glutathione S-tranferase and maltose E binding protein, respectively, to the target recombinant protein. Accordingly, a nucleic acid molecule encoding a bcl-$X_L$ protein may be linked to additional coding sequences in a procaryotic fusion vector to aid in the expression, solubility or purification of the fusion protein. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase.

Inducible non-fusion expression vectors include pTrc (Amann et. al., (1988) *Gene* 69:301–315) and pET 11d (Studier et. al., *Gene Expression Technology: Methods in Enzymology* 185, Academic Press, San Diego, Calif. (1990) 60–89). Target gene expression from the pTrc vector4 relies on host RNA polymerase transcription from the hybrid trp-lac fusion promoter. Target gene expression from the pET 11d vector relies on transcription from the T7 gn10-lac 0 fusion promoter mediated by a coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize expression of a bcl-$X_L$ protein in E. coli is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleotide sequence of the nucleic acid molecule encoding bcl-$X_L$ protein to be inserted into an expression vector so that the individual codons for each amino acid would be those preferentially utilized in highly expressed E. coli proteins (Wada et al, (1992) *Nuc. Acids Res.* 20:2111–2118). Such alteration of nucleic acid sequences are encompassed by the invention and can be carried out by standard DNA synthesis techniques.

Alternatively, a bcl-$X_L$ protein can be expressed in a eucaryotic host cell, such as a mammalian cell (e.g., Chinese hamster ovary cells (CHO) or NSO cells), insect cells (e.g., using a baculovirus vector) or yeast cells. Other suitable host cells may be found in Goeddel, (1990) supra, or are known to those skilled in the art. Eucaryotic, rather than procaryotic, expression of a bcl-$X_L$ protein may be preferable since expression of eucaryotic proteins in eucaryotic cells can lead to partial or complete glycosylation and/or formation of relevant inter- or intra-chain disulfide bonds of a recombinant protein. For expression in mammalian cells, the expression vector's control functions are often provided by viral material. For example, commonly used promoters are derived from polyoma, Adenovirus 2, cytomegalovirus and Simian Virus 40. To express a bcl-$X_L$ protein in mammalian cells, generally COS cells (Gluzman, Y., (1981) *Cell*

23:175–182) are used in conjunction with such vectors as pCDM8 (Seed, B., (1987) *Nature* 329:840) for transient amplification/expression, while CHO (dhfr⁻ Chinese Hamster Ovary) cells are used with vectors such as pMT2PC (Kaufman et al (1987), *EMBO J* 6:187–195) for stable amplification/expression in mammalian cells. A preferred cell line for production of recombinant protein is the NSO myeloma cell line available from the ECACC (catalog #85110503) and described in Galfre, G. and Milstein, C. ((1981) *Methods in Enzymology* 73(13):3–46; and *Preparation of Monoclonal Antibodies: Strategies and Procedures*, Academic Press, N.Y., N.Y.). Examples of vectors suitable for expression of recombinant proteins in yeast (e.g., *S. cerivisae*) include pYepSecl (Baldari. et al, (1987) *Embo J.* 6:229–234), pMFa (Kurjan and Herskowitz, (1982) *Cell* 30:933–943), pJRY88 (Schultz et. al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

Vector DNA can be introduced into procaryotic or eucaryotic cells via conventional transformation or transfection techniques such as calcium phosphate or calcium chloride co-precipitation, DEAE-dextran-mediated transfection, lipofection, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks.

For stable transfection of mammalian cells, it is known that, depending upon the expression vector and transfection technique used, only a small faction of cells may integrate DNA into their genomes. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same plasmid as the gene of interest or may be introduced on a separate plasmid. Cells containing the gene of interest can be identified by drug selection (e.g., cells that have incorporated the selectable marker gene will survive, while the other cells die). The surviving cells can then be screened for production of bcl-$X_L$ proteins by, for example, immunoprecipitation from cell supernatant with an anti-bcl-$X_L$ antibody.

bcl-$X_L$ proteins produced by recombinant technique may be secreted and isolated from a mixture of cells and medium containing the protein. For secretion of bcl-$X_L$ protein, a DNA sequence encoding an appropriate signal peptide is linked to the 5' end of the nucleotide sequence encoding bcl-$X_L$, such that bcl-$X_L$ protein is linked to the signal peptide that will result in secretion of the protein from the cell. Alternatively, the protein may be retained cytoplasmically and the cells harvested, lysed and the protein isolated. A cell culture typically includes host cells, media and other byproducts. Suitable mediums for cell culture are well known in the art. Protein can be isolated from cell culture medium, host cells, or both using techniques known in the art for purifying proteins.

The recombinantly produced bcl-$X_L$ protein can then be packaged in a suitable pharmaceutical vehicle for administration into a subject, such that bcl-$X_L$ protein is introduced into the T cells of the subject resulting in protection of the T cells against cell death. Suitable vehicles for administration into a subject are described herein. For in vivo and ex vivo introduction of the recombinant bcl-$X_L$ protein into T cells, the recombinant protein is preferable packaged in liposomes. However other carrier systems can be used.

In other embodiments of the method, T cell survival is enhanced by reducing protein levels of antagonists of bcl-$X_L$, such as the proteins bcl-$X_S$ of Bad. Reducing protein levels of bcl-$X_L$ antagonists can be accomplished by contacting the T cell with at least one agent which decreases expression of the genes encoding the antagonists or by introducing into the T cell a nucleic acid or other compound that will decrease levels of biologically active antagonists. Methods for downregulating bcl-$X_S$ and Bad protein levels can be adapted from the methods described herein for downregulating bcl-$X_L$ protein levels.

To reduce T cell death, any of the above-described methods can be combined.

2. Methods for Rendering a T Cell Susceptible to Cell Death

In a specific embodiment of the invention, a T cell is rendered more susceptible to cell by inhibiting or decreasing the level of bcl-$X_L$ protein in the T cell. For example, the susceptibility of a T cell to cell death can be increased by contacting the T cell with an agent which inactivates bcl-$X_L$ function or reduces the biological activity of bcl-$X_L$. The language "rendering a T cell susceptible to cell death" is intended to include modifying a T cell such that the amount of biologically active bcl-$X_L$ protein, in the T cell is reduced such that the susceptibility of the T cell to cell death is increased as compared to a non-modified T cell. The terms "functional bcl-$X_L$ protein" and "biologically active bcl-$X_L$ protein" is intended to include wildtype bcl-$X_L$ protein, or alternatively any modified form of bcl-$X_L$ protein that is capable of performing the biological function of the wildtype bcl-$X_L$ protein. The method of the invention for rendering a T cell susceptible to cell death has numerous therapeutic applications wherein it is desirable to delete a polyclonal population of T cells, or a specific T cell clone. Thus, the method of the invention is useful, for example, in the treatment of autoimmune diseases.

Methods for reducing bcl-$X_L$ protein levels in a T cell include methods comprising contacting a T cell with an agent which decreases the level of transcription of the bcl-X gene, an agent which destabilizes bcl-$X_L$ mRNA, an agent which blocks splicing of the bcl-X premRNA into the bcl-$X_L$ mRNA, an agent which blocks translation of the mRNA, or any combination of these agents. Alternatively the protective effect of bcl-$X_L$ protein can be overcome by increasing the protein level of a protein which interacts with bcl-$X_L$ and inhibits or decreases the biological activity of bcl-$X_L$. In one embodiment, the protein level of Bad or bcl-$X_S$ protein is increased in the T cell, such that T cells are rendered more susceptible to cell death.

In a specific embodiment of the invention, bcl-$X_L$ protein levels in a T cell are reduced by introducing into the T cell a nucleic acid expressing either an RNA or a protein that interferes with bcl-$X_L$ function. For example, one embodiment, antisense nucleic acids that inhibit production of bcl-$X_L$ protein are introduced into the T cells. An "antisense" nucleic acid comprises a nucleotide sequence which is complementary to a "sense" nucleic acid, e.g., complementary to an mRNA sequence encoding a protein, constructed according to the rules of Watson and Crick base pairing. Accordingly, an antisense nucleic acid can hydrogen bond to a sense nucleic acid. An antisense sequence complementary to a sequence of an mRNA can be complementary to a sequence found in the coding region of the mRNA or can be complementary to a 5' or 3' untranslated region of the mRNA. The coding region of a nucleotide sequence encoding a human bcl-$X_L$ shown in SEQ NO: 1. Preferably, an antisense nucleic acid is complementary to a region preceding or spanning the initiation codon or in the 3' untranslated region of an mRNA. An antisense nucleic acid can be designed based upon the nucleotide sequence shown in SEQ ID NO: 1. or other bcl-$X_L$-encoding sequence known in the art. For example, a nucleic acid is designed which has a sequence complementary to the coding or untranslated region of the nucleotide sequence of SEQ ID NO: 1.

An antisense nucleic acid of the invention can be constructed using chemical synthesis and enzymatic ligation reactions using procedures known in the art. The antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Antisense oligonucleotides can be introduced into a T cell in culture to inhibit expression of a bcl-$X_L$. One or more antisense nucleic acids, such as oligonucleotides, can be added to cells in culture media, typically at about 200 μg/ml.

Alternatively, the antisense nucleic acid can be produced biologically in the T cell using an expression vector into which a nucleic acid corresponding to at least a fragment of a nucleotide sequence encoding a bcl-$X_L$ protein has been subcloned in an antisense orientation (i.e., RNA transcribed from the inserted nucleic acid will be of an antisense orientation to a target nucleic acid of interest). The antisense expression vector can be in the form of a recombinant plasmid, phagemid or attenuated virus in which antisense nucleic acids are produced under the control of a high efficiency regulatory region. The regulatory region can stimulate constitutive or inducible expression of the nucleic acid molecule. The regulatory regions controlling the expression of the nucleic acid molecule, and the vectors that carry such sequences, as well as methods for introducing the nucleic acid molecule into the T cells have been described above. A nucleic acid molecule encoding a bcl-$X_L$ antisense mRNA can be introduced into T cells ex vivo, or in vivo. Methods for introducing nucleic acids into T cells in vivo are as described above. For a discussion of the regulation of gene expression using antisense genes see Weintraub, H. et al., Antisense RNA as a molecular tool for genetic analysis, Reviews—Trends in Genetics, Vol. 1(1) 1986.

In another embodiment of the invention, bcl-$X_L$ protein levels in a T cell are reduced by introducing into the T cell a nucleic acid encoding a form of antisense nucleic acid which is a ribozyme. Ribozymes are catalytic RNA molecules with ribonuclease activity which are capable of cleaving a single-stranded nucleic acid, such as an mRNA, to which they have a complementary region. A ribozyme having specificity for a bcl-$X_L$-encoding sequence can be designed based upon the nucleotide sequence of a bcl-$X_L$-encoding mRNA. For example, a derivative of a Tetrahymena L-19 IVS RNA can be constructed in which the base sequence of the active site is complementary to the base sequence to be cleaved in a bcl-$X_L$-encoding mRNA. See for example Cech et al. U.S. Pat. No. 4,987,071; and Cech et al. U.S. Pat. No. 5,116,742. Alternatively, a bcl-$X_L$-encoding sequence can be used to select a catalytic RNA having a specific ribonuclease activity from a pool of RNA molecules. See for example Bartel, D. and Szostak, J. W. (1993) *Science* 261: 1411–1418.

In yet another embodiment of the method, a T cell is rendered susceptible to cell death by reducing the level of bcl-$X_L$ protein by introducing into the T cell a nucleic acid molecule encoding an inhibitory protein which interacts with bcl-$X_L$ and inhibits the biological function of bcl-$X_L$. In a specific embodiment of the invention, the inhibitory protein is Bad or a fragment thereof that is capable of decreasing the biological activity of bcl-$X_L$ (Yang, E. et al. (1995) *Cell* 80, 285). In another embodiment, the inhibitory protein is an intracellular antibody that interacts with bcl-$X_L$. Intracellular antibody molecules can be introduced into a T cell by a method comprising introducing and expressing in the T cell a single chain antibody molecule according to the methods described herein. Such a method is for example described in Biocca, S. et al. (1993) *Biochemical and Biophysical Research Communications* 197, 422; Biocca, S. et al. (1994) *Bio/Technology* 12, 396; Marasco, W. A., et al. (1993) *Proc. Natl. Acad. Sci USA* 90, pp. 7889; and Werge et al. (1990) *FEBS* 274, 193.

In another embodiment of the invention, bcl-$X_L$ protein level in a T cell is decreased by contacting the T cell with an agent which downregulates endogenous bcl-$X_L$ protein levels. In a specific embodiment, the agent decreases transcription of the bcl-$X_L$ gene. Agents that downregulate bcl-$X_L$ protein levels in T cell can be identified using an assay in which the agent to be tested is incubated with the T cells and bcl-$X_L$ protein levels are determined by Western blot analysis as described herein.

Also within the scope of the invention are methods for rendering T cells more susceptible to cell death by augmenting the level of an antagonist of bcl-$X_L$, such as bcl-$X_S$ or Bad. The protein level of either or both of these proteins can be increased in a T cell by contacting the T cell with an agent which, for example, stimulates the expression of the genes encoding bcl-$X_S$ or/and Bad. In one embodiment, the agent which stimulates expression of the bcl-X gene encoding bcl-$X_S$ does not stimulate the production of bcl-$X_L$. Alternatively, a nucleic acid encoding these proteins can be introduced into T cells by methods similar to those described for augmenting bcl-$X_L$ protein levels. Nucleic acid sequences encoding antagonists of bcl-$X_L$ are disclosed, for example, in Yang, E., et al. (1995) *Cell* 80, 285. Methods for increasing bcl-$X_S$ or Bad protein levels in a cell can be adapted from the methods described herein for increasing bcl-$X_L$ protein levels.

In one embodiment of the invention, T cells are rendered susceptible to cell death by contacting the T cells with an agent which decreases bcl-$X_L$ protein levels in the T cell together with an agent which provides a primary T cell activating signal to thereby stimulate T cell death. The agent which provides a primary activating signal can be a polyclonal activator, such as an anti-CD3 antibody. In a preferred embodiment of the invention, the agent which provides a primary activating signal is an antigen on an antigen presenting cell. In yet another embodiment of the invention, the T cell is further contacted with additional antigens on antigen presenting cell, such that at least one T cell clone is rendered susceptible to cell death. In a further embodiment, the T cells are further contacted with agents which block costimulatory signals. Thus, in one embodiment of the invention, T cell death is induced by stimulating a primary activating signal in the T cells, inhibiting costimulation of the T cells, and reducing bcl-$X_L$ protein levels in the T cell according to the method of the invention. The method of the invention thus allows for inducing T cell death of a polyclonal population of T cells or alternatively for inducing T cell death of a restricted number of T cell clones (e.g. antigen-specific T cell clones within a population of T cells).

Any of the above described methods for increasing the susceptibility of a T cell to cell death may be combined.

3. Pharmaceutical Compositions

The invention pertains to methods for protecting a T cell from cell death by augmenting bcl-$X_L$ protein levels in the T cell. Augmentation of the level of bcl-$X_L$ in a T cell can be accomplished by augmenting the level of the endogenous bcl-$X_L$ protein or by introducing into the T cell a nucleic acid encoding a bcl-$X_L$ protein, or a combination of both. In a specific embodiment, the level of the endogenous bcl-$X_L$ protein is augmented by contacting the T cell with an agent which acts intracellularly. In another embodiment of the invention, the susceptibility of a T cell to cell death is increased by contacting the T cell with an agent which reduces bcl-$X_L$ protein levels in the T cell. The methods of the invention can be practiced in vivo, ex vivo, or by a combination of both. For practicing the methods of the invention ex vivo, a population of T cells is obtained from a subject, contacted in vitro with an agent which augments or reduces bcl-$X_L$ protein levels, and, if desired, readministered to the subject (this embodiment is further described below). The level of bcl-$X_L$ protein can be monitored by Western blot analysis, as described herein.

For practicing the methods of the invention in vivo, the agents are administered to the subjects in a biologically compatible form suitable for pharmaceutical administration in vivo. By "biologically compatible form suitable for administration in vivo" is meant a form of the agent to be administered in which any toxic effects are outweighed by the therapeutic effects of the agent. Agents to be administered include nucleic acid molecules encoding bcl-$X_L$ proteins or encoding antisense nucleic acid molecules to inhibit production of bcl-$X_L$ protein in the cell, agents which act intracellularly to augment or reduce bcl-$X_L$ protein level, and agents which regulate an inducible control element operably linked to a nucleic acid molecule encoding a bcl-$X_L$ protein or operably linked to a nucleic acid molecule encoding bcl-$X_L$ antisense nucleic acid molecules.

The term "subject" is intended to include living organisms in which an immune response can be elicited, e.g., mammals. Examples of subjects include humans, dogs, cats, mice, rats, and transgenic species thereof. For example, animals within the scope of the invention include animals of agricultural interest, such as livestock and fowl. Alternatively, the methods of the invention can also be applied to plants.

Administration of a therapeutically active amount of an agent of the present invention is defined as an amount effective, at dosages and for periods of time necessary to achieve the desired result. For example, a therapeutically active amount of an agent may vary according to factors such as the disease state, age, sex, and weight of the subject, and the ability of the agent to elicit a desired response in the subject. Dosage regimens may be adjusted to provide the optimum therapeutic response. For example, several divided doses may be administered daily or the dose may be proportionally reduced as indicated by the exigencies of the therapeutic situation.

The agent may be administered in a convenient manner such as by injection (subcutaneous, intravenous, etc.), oral administration, inhalation, transdermal application, or rectal administration. Depending on the route of administration, the agent may be coated in a material to protect it from the action of enzymes, acids and other natural conditions which may inactivate the agent.

To administer an agent by other than parenteral administration, it may be necessary to coat the agent with, or co-administer the agent with, a material to prevent its inactivation. For example, an expression plasmid comprising a nucleic acid molecule encoding a bcl-$X_L$ protein may be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) J. Neuroimmunol 7:27). Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

When the agent is suitably protected, as described above, it may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the agent, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the agent and the particular therapeutic effect to be achieved, and (b) the limitations inherent in the art of compounding such an agent for the treatment of sensitivity in subjects.

4. Applications for the Methods of the Invention

The invention pertains to methods for protecting a T cell from cell death by augmenting the level of bcl-$X_L$ protein in the T cell. The invention also pertains to methods for rendering a T cell susceptible to cell death by decreasing the level of bcl-$X_L$ protein in the T cell. These methods can be practiced either in vivo and ex vivo. When practiced ex vivo, peripheral blood mononuclear cells can be obtained from an subject and isolated by density gradient centrifugation, e.g., Ficoll/Hypaque. In a specific embodiment, the purified peripheral blood cells are then contacted with an agent that modulates the level of bcl-$X_L$ protein. In other embodiments of the method, the peripheral blood mononuclear cells are further enriched in specific cell types prior to being contacted with the agent which modulates the level of bcl-$X_L$ protein. Monocytes can be depleted, for example, by adherence on plastic. If desired, the CD4$^+$T cell population can further be enriched by separation from residual monocytes, B cells, NK cells and CD8$^+$T cells using monoclonal antibody (mAb) and anti-mouse-Ig coated magnetic beads using commercially available mAbs (such as anti-CD14 (Mo2), anti-CD11b (Mo1), anti-CD20 (B1), anti-CD16 (3G8) and anti-CD8 (7PT 3F9) mAbs). The method of the invention can also be applied to subsets of CD4+T cells, such as CD4$^+$CD45RA$^+$ (naive CD4+T cells) and CD4$^+$CD45RO$^+$ (memory T cells) T cell subsets. These can be prepared as described above, with the additional use of anti-CD45RO antibody (UCHLI) for the preparation of the CD4$^+$ CD45RA$^+$cells and the addition of anti-CD45RA antibody (2H4) for the preparation of the CD4$^+$CD45RO$^+$T cells.

The efficiency of the purification can be analyzed by flow cytometry (Coulter, EPICS Elite), using anti-CD3, anti-CD4, anti-CD8, anti-CD14 mAbs, or additional antibodies that recognize specific subsets of T cells, followed by fluorescein isothiocyanate conjugated goat anti mouse immunoglobulin (Fisher, Pittsburgh, Pa.) or other secondary antibody.

The type of cell population used ex vivo will depend on various factors including the type of agent used for modulating bcl-$X_L$ protein levels, the type of vehicle used to deliver the agent to the T cells, and the subset of T cells in which it is desirable to augment bcl-$X_L$ protein level. Thus, when an agent specifically affects a subset of T cells (e.g. by use of a delivery vehicle that targets only a specific subset of T cells) purification of the specific subset of T cells is not required. Vehicles that allow targeting of the agent to specific subsets of cells include liposomes or recombinant viral particles to which molecules that specifically recognize the desired cell type are linked. Such molecules include antibodies to surface molecules or ligands to receptors. If only a selective subset of T cells is desired to be targeted, e.g., CD4+T cells, and the agent used is not capable of targeting selectively this subset of T cells, it may be necessary to isolate the specific subset of T cells prior to contacting the cells with the agent.

The peripheral blood cells, or purified subset thereof, such as T cells obtained from the subject are then incubated in vitro in the presence of the agent which modulates the level of bcl-$X_L$ protein in T cells. The amount of agent will depend on various factors, such as the type of agent, the effect desired, and the population of cells contacted with the agent. The appropriate amount of agent to be added to the population of cells can be determined by performing assays in which various doses of agent are added to the cell culture and the amount of bcl-$X_L$ protein is determined at various time points by Western blot analysis, as described herein. If a heterologous population of cells is contacted with the agent, it may be necessary to first isolate the subset of T cells in which bcl-$X_L$ is desired to be modulated prior to subjecting the cells to Western blot analysis. Specific subsets of T cells can be isolated from a population of cells by negative selection, as described above, or alternatively a specific subset of T cells can be isolated by using FACS.

In a specific embodiment of the invention, T cells isolated from a subject are contacted with an agent which modulates the protein level of bcl-$X_L$ and further cultured in vitro to expand the population of T cells (i.e., increase the number of T cells within the population). In vitro expansion of a population of T cells obtained from a subject can be performed as described in the published PCT Application Number WO 94/29436, the contents of which are incorporated herein by reference.

Following modulation of bcl-$X_L$ protein levels in the T cells, or subset thereof, the cells can be readministered to a subject. In a specific embodiment, the cells are first purified to remove any agent in the culture medium that is undesirable to administer to the subject. Purification can be performed, for example, by Ficoll Hypaque gradient centrifugation.

Alternatively, the method of the invention can be practiced in vivo. In this embodiment, the agent which modulates bcl-$X_L$ protein level in T cells is administered to a subject in a physiologically acceptable vehicle and in an amount sufficient to obtain the desired therapeutic effect. The agent is administered locally or systemically depending on the type of condition to be treated by the method of the invention. Suitable vehicles for administration of the agents and routes of administration are described in the Section 3 of the present specification.

4.1. Application of the Method of the Invention to Conditions Benefiting from Protection Against T Cell Death The methods of the invention are useful for preventing cell death of T cells. According to the method of the invention, cell death can be prevented in all T cells, or alternatively, cell death can be selectively prevented in a specific subset of T cells. Furthermore, T cells can be protected from cell death for an extended period of time, or alternatively for a short period of time. T cells present locally, or T cells present systemically (e.g. in the peripheral blood) can be protected from cell death.

In a preferred embodiment, the method of the invention is used for preventing cell death of CD4+T cells of an HIV infected individual and protecting T cells from HIV infection. During HIV infection, the virus infects and kills CD4+T cells. Thus, the number of CD4+T cells in the individual progressively decreases to numbers insufficient for preventing infection of the subject by microorganisms. It has been observed that T cells in which the level of bcl-$X_L$ protein has been increased show significant protection against infection by HIV as measured by increased viability of the T cells (see Example 9). Thus, increasing the level of bcl-$X_L$ protein in T cells protects the T cells from HIV induced cell death. Hence bcl-$X_L$ overexpression in T cells provides an efficient method for maintaining the number of CD4+T cells in an HIV infected subject. Moreover, the method of the invention may result in increased numbers of CD4+T cells in an HIV infected subject, and/or a reduced rate of T cell depletion in an HIV infected individual.

The method of the invention provides for methods that allow expansion of a population of T cells from an individual having a T cell associated disorder, such as an infection with HIV, or other infectious agent which renders the T cells susceptible to cell death. Thus, the method provides a method for expanding the cells in vitro. The expanded T cell population can then be administered back to the subject. In a preferred embodiment, the T cells are stimulated with a combination of agents providing a primary activation signal to the T cells and an agent which provides a costimulatory signal to the T cell. In a much preferred embodiment, the T cells are cultured with a combination of an agent that interacts with CD28 on the T cell and an agent that stimulates the T cells through the T cell receptor, such that the bcl-$X_L$ protein level is increased and the cells are protected from cell death.

In a specific embodiment of the invention for preventing T cell death in an HIV infected subject, peripheral blood cells are obtained from the subject, modified in vitro to increase the amount of bcl-$X_L$ protein in the CD4+T cells and readministered to the individual. In a preferred embodiment of the invention, the CD4+T cells from the subject are modified to contain an increased level of bcl-$X_L$ protein by introducing into the T cells a nucleic acid molecule encoding a bcl-$X_L$ protein. In an even more preferred embodiment, the nucleic acid molecule encoding bcl-$X_L$ is contained within a viral vector introduced into the T cells by methods such as infection of the cells with the viral particle. In another preferred embodiment of the method, the CD4+T cells are further expanded in culture prior to readministration into the subject. Thus, the method of the invention allows for repopulating the immune system of a subject infected with HIV with CD4+T cells and simultaneously rendering these CD4+T cells resistant to infection by the virus.

It is also possible to protect the CD4+T cells of a subject infected with HIV from cell death by administrating to the subject an agent which increases the level of bcl-$X_L$ protein in the CD4+T cells of the individual. The agent can be a nucleic acid molecule encoding a bcl-$X_L$ protein comprised in a physiologically acceptable vehicle. In a more preferred embodiment of the invention, the vehicle is further engineered to target the nucleic acid specifically to CD4+T cells. Alternatively, the agent is an agent which acts intracellularly to increase bcl-$X_L$ protein levels in CD4+T cells.

In another embodiment, the T cells of a subject infected with HIV are protected from cell death by a method combining the ex vivo and in vivo methods described above. The method can also comprise contacting the CD4+T cell of the individual in vivo and/or ex vivo with several agents which augment bcl-$X_L$ protein level. For example, a nucleic acid encoding a bcl-$X_L$ protein is introduced into the T cells and the T cells are further contacted with an agent which acts intracellularly to increase the level of endogenous bcl-$X_L$ protein.

Alternatively, the method of the invention is useful for boosting an immune reaction in order to more eliminate rapidly an infection. Thus, in a specific embodiment of the method, activated T cells are protected from cell death by contacting them with an agent which augments bcl-$X_L$ protein level in the T cells, such that they are protected from cell death. Protecting CD4+T cells from cell death following activation of the T cell will allow the helper T cell to provide "help" to more effector cells than the T helper cell would normally be able to provide. Similarly, a CD8+T cell which has an extended life span will be able to lyse more target cells than a CD8+T cell with a normal life span. Methods within the scope of the invention are methods for treating systemic infections and local infections. Thus, the agent can be administered systemically or locally. In a preferred embodiment of the invention, the agent which augments bcl-$X_L$ protein level in T cells is an agent which acts intracellularly to augment bcl-$X_L$ protein level. In an even more preferred embodiment of the invention, the agent is an agent which has a short half-time, such that the life span of the activated T cell is not prolonged for times longer than necessary (e.g. the activated T cell becomes a memory T cell or dies following clearance of the infection).

4.2. Application of the Method of the Invention to Conditions Benefiting from Increased Susceptibility to T Cell Death The methods of the invention are also useful for increasing the susceptibility of T cells to cell death. Thus, a T cell which encounters conditions in which it normally would be protected from cell death due to an increase in endogenous bcl-$X_L$ protein levels, will die if the level of bcl-$X_L$ protein in the T cell is significantly decreased. The method of the invention is useful for treating a subject with a T cell associated disorder. "T cell associated disorder" is intended to mean a disorder associated with T cells having an extended lifespan.

In a specific embodiment, the method of the invention is used for treating an autoimmune disease in a subject. Susceptibility to cell death is increased in autoreactive T cells to ameliorate the effects of the autoimmune disease. Examples of autoimmune diseases which may be treated include multiple sclerosis, insulin dependent diabetes mellitus, arthritis (e.g., rheumatoid arthritis, juvenile rheumatoid arthritis, osteoarthritis), myesthenia gravis, myocarditis, Guillan-Barre Syndrome, systemic lupus erythematosis, autoimmune thyroiditis, dermatitis, psoriasis, Sjögren's Syndrome, alopecia areata, Crohn's disease, aphthous ulcer, iritis, conjunctivitis, keratoconjunctivitis, ulcerative colitis, allergy, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, and interstitial lung fibrosis.

In another embodiment, the method of the invention is used to reduce graft rejection. For example, graft cells are administered to the host together with an agent which reduces bcl-$X_L$ protein levels in T cells, such that T cells reactive against graft cells are rendered more susceptible to cell death. The method can further comprise administering to the host an agent which blocks costimulation, such as CTLA4Ig. Similarly, the method of the invention can also be used to prevent graft versus host disease. In a preferred method, donor bone marrow is contacted prior to transplantation with host cells and an agent which reduces bcl-$X_L$ protein level in T cells. Thus, T cells in the donor bone marrow are rendered more susceptible to cell death, and in combination with agents which inhibit costimulation, can increase cell death of T cells reactive to host specific antigens.

The following invention is further illustrated by the following examples, which should not be construed as further limiting. The contents of all references, pending patent applications and published patents, cited throughout this application are hereby expressly incorporated by reference.

EXAMPLES

Example 1

Activation Enhances T cell Survival Following γ-irradiation

To study the effects of T cell activation pathways on T cell survival, resting T cells were isolated from human peripheral blood by negative selection as previously described (June, C. H. et al. (1987) *Mol. Cell. Biol.* 7:4472–4481). Briefly, cells were subjected to a cocktail of antibodies to remove all cells except resting CD28-positive T cells. T cells were cultured in RPMI 1640 supplemented with fetal calf serum (10%), L-glutamine (2 mM), penicillin/streptomycin (100 U/ml, 100 μg/ml), and HEPES (20 mM). Cells were rested overnight prior to activation or irradiation.

CD28+T cells were cultured in medium alone or stimulated by crosslinking the TCR/CD3 complex in the presence or absence of costimulation provided by a CD28-specific monoclonal antibody for 12 hours Crosslinking of the T cell receptor was performed using plate-immobilized anti-CD3 (G19.4 [at 1 μg/ml]) and costimulation of the T cells was performed with soluble antibody to CD28 (monoclonal antibody (mAb) 9.3) at 1 μg/ml. Cells from each of these groups were then split into groups. One group was cultured without further manipulation, while the other group was subjected to 15 Gy of γ-irradiation with a cesium source γ-irradiator (J. L. Shepherd Inc.). Following irradiation, cells were plated at 100,000 cells/well in 96 well cultures dishes (Costar) and viability and total cell numbers were assessed by trypan blue exclusion and propidium iodide exclusion.

For propidium iodide exclusion, two separate samples of $2\times10^5$ cells were pelleted and resuspended in 0.5 ml of PBS supplemented with 1% BSA and 0.01% sodium azide. Two ml of propidium iodide (0.5 mg/ml) was then added to the cells and samples were then analyzed by FACS using a FACSort and Lysis II software. Percent viability was determined by dividing the number of cells which excluded propidium iodide (viable) by the total number of cells. Forward light scatter characteristics of living cells was utilized to delete debris from the analyses.

The results are presented graphically in FIG. 1. All 3 populations of cells maintained high viability over the 4 day culture period (FIG. 1 panel A). The survival of resting and activated T cells was also examined following exposure to γ-irradiation (FIG. 1 panel B). γ-irradiation-induced apoptosis does not require a specific receptor ligand interaction and thus can be considered as a tool to study how cell activation influences cell survival without the need to control for specific receptor levels. The dose used in these assays (15 Gy) is sufficient to induce lethal DNA damage in virtually all cells in the population. Thus, the rate at which the cells die over the ensuing days can be used as a measure of their ability to resist undergoing PCD in response to DNA damage.

FIG. 1, panel B indicates that, following irradiation, the viability of resting T cells declined much more rapidly than it did in either population of stimulated lymphocytes. At four days post-irradiation, T cells in either activated population were statistically more likely to be alive than cells in the resting population (p<0.02). Cells costimulated through the CD28 receptor demonstrated a slight, but reproducible, enhancement in survival over cells stimulated with anti-CD3 alone. The maintenance of cell viability in anti-CD3 stimulated and anti-CD3+anti-CD28 stimulated cells was not the result of subsequent T cell proliferation as cell counts done in parallel to the viability assays revealed that the absolute cell number did not change. Furthermore, all the cells in the activated populations were arrested within the cell cycle at either late $G_1$ or $G_2$. Cell death in all three populations followed a classic apoptotic pattern with cells first becoming crenated, followed by nuclear condensation and DNA fragmentation.

Thus, this example indicates that activation of T cells enhances their survival following γ-irradiation.

Example 2

CD28 Costimulation Augments the Survival of anti-CD3-activated T Cells

One difference between cells stimulated in the presence or absence of CD28 costimulation is the level of lymphokines produced by these cells (Lindsten, T. et al. (1989) *Science* 244:339–343). Previous evidence has suggested that growth factors play an important role in the extrinsic regulation of cell survival in a variety of cell types (Groux, H. et al. (1993) *Eur. J. Immunol.* 23:1623–1629), Nuñez, G. et al (1990) *J. Immunol.* 144:3602–3610). To determine if growth factors were responsible for the protective effect of costimulation, the following example was performed.

CD28+T cells were cultured for 12 hours in the presence of an anti-CD3 antibody in the presence or absence of costimulation with an anti-CD28 monoclonal antibody, as described in Example 1. The cells were then either left in their conditioned medium, washed and resuspended in fresh medium, or washed and resuspended in fresh medium supplemented with 200 u/ml of recombinant IL-2 (rIL-2) (Boehringer-Mannheim). Aliquots from each group were then left unmanipulated or subjected to 15 Gy or γ-irradiation. Cell viability was determined by propidium iodide exclusion, daily for 4 days following manipulation, as described in Example 1.

The results are presented graphically in FIG. 2. Panel A of FIG. 2 indicates that T cells activated through the TCR/CD3 complex alone maintained high viability in culture following activation. However, removal of conditioned medium by washing the stimulated cells led to a marked reduction in the ability of the cells to survive in culture. This reduced ability to survive in in vitro culture can be completely reversed by addition of IL-2. When anti-CD3-stimulated cells were subjected to 15 Gy of γ-irradiation (FIG. 2 panel B), the removal of conditioned medium after overnight stimulation led to a sharp reduction in cell viability which was reversed by the addition of IL-2. This shows that survival is primarily determined by the levels of extrinsic growth factors in antigen receptor-activated cells. The ability of activated T cells to survive in culture is therefore based on their autocrine ability to produce growth factors such as IL-2. These data confirm that IL-2 is an extrinsic regulator of T cell survival.

In contrast to these results observed with T cells stimulated through the TCR/CD3 complex alone, T cells stimulated with a combination of anti-CD3+anti-CD28 do not differ in their survival neither when washed free of endogenously produced lymphokines nor when further IL-2 is added to the culture supernatants (FIG. 2 panels C and D).

The results of this example demonstrated that CD28-mediated costimulation may not only affect the production of extrinsic mediators of cell survival, but also play a role in regulating the intrinsic susceptibility of cells to undergo PCD (examined further in subsequent example).

Example 3 bcl-2 and bcl-X mRNA Expression During T Cell Activation

To investigate the role of CD28 in regulating the expression of genes involved in intrinsic resistance of T cells to undergo PCD, the level of expression of bcl-X and bcl-2 was analyzed in resting human T cells and T cells activated by crosslinking of the TCR antigen receptor complex in the presence or absence of anti-CD28.

RNA was isolated from CD28+T cells cultured in medium alone, or following stimulation with anti-CD3 or anti-CD3 and anti-CD28 for 1, 6 and 12 hours and analyzed by Northern blot hybridization. RNA was isolated from the T cells by centrifugation through guanidium/CsCl$_2$ gradients as previously described (June, C. H. et al. (1987) *Mol. Cell. Biol.* 7:4472–4481). Equal amounts of RNA (as assessed by ethidium bromide staining of 28 S ribosomal RNA electrophoresed on non-denaturing agarose gels) were loaded onto agarose/formaldehyde denaturing gels and separated by size. Gels were transferred to nitrocellulose (Schleicher and Schuell) and baked under vacuum for 2 hr at 80° C. Blots were prehybridized at 42° C. for 6 hrs in Stark's solution (50% Formamide, 5×SSC (1×SSC is 0.15 M NaCl, 0.015 M sodium citrate), 1×Denhardt's solution, 25 mM sodium phosphate, pH 6.5, 250 µg Torula RNA per ml) and hybridized in Stark's solution with 10% dextran sulfate and $^{32}$P-labelled nick translated probes (1×10$^6$ dpm/ml) overnight at 42° C. The blots were probed and stripped sequentially with probes specific for human bcl-X$_L$ cDNA and murine bcl-2 cDNA (S. Korsmeyer).

The results of the Northern blot hybridization are represented in FIG. 3 panel A. The results show that neither bcl-X nor bcl-2 mRNA is expressed at detectable levels in resting T cells. However, the expression of both bcl-2 and bcl-X mRNA is induced within 6 hours after T cell activation. CD28 costimulation had no significant effect on the expression of bcl-2 mRNA. In contrast, CD28 costimulation enhanced the expression of bcl-X mRNA. Cells stimulated with anti-CD3 and anti-CD28 maintained high level expression of bcl-X for 48 hours after which levels began to decline. A third member of the bcl-2 family thought to have a negative role in regulating the function of bcl-2 is the gene bax. Costimulation also had no affect on bax mRNA levels.

Alternative usage of the two 5' splice donors in the first exon of bcl-X can yield two distinct mRNA species. bcl-X$_L$ retains the full coding region of exon 1 and functions to enhance cell survival. In contrast, use of an upstream splice donor site within exon 1 results in the bcl-X$_S$ mRNA which contains a 189 bp deletion within the exon 1 coding region. The Bcl-x$_S$ protein acts as a dominant negative regulator of both Bcl-2 and bcl-X$_L$ functions (Boise, L. H. et al. (1993) *Cell* 74:597–608). Since the bcl-X$_S$ and bcl-X$_L$ mRNAs differ by only 189 bp, RNase protection was performed to determine which bcl-X mRNA was induced upon T cell activation and costimulation.

Rnase protection assays were performed on RNA isolated from T cells that were either resting, or stimulated for 6 or 12 hours with anti-CD3 or anti-CD3 and anti-CD28. RNase protection analysis (RPA) was performed according to the specifications of a commercially available kit (Ambion). 3 µg of T cell RNA was hybridized to a radiolabelled riboprobe that was generated by cutting the bcl-X$_L$ cDNA in pBluesript SK+ plasmid with AccI and generating transcripts in vitro from the T3 promoter using a kit from Promega. The 336 nucleotide riboprobe was purified by gel electrophoresis, extracted and hybridized to T cell RNA for 16 hr at 42° C. prior to the addition of a cocktail of RNaseA and RNaseT1. Protection of the probe by bcl-X$_L$ mRNA yields a fragment of 264 nucleotides, while hybridization to the bcl-X$_S$ message protects a 163 nucleotide fragment of the radiolabelled probe. Protection products were separated on 5% acrylamide/7M urea sequencing gel. End-labelled pBluescript SKII+ digested with HpaII was used as a marker. Gels were dried down and exposed to XAR-5 film (Kodak).

The results of the Rnase protection assay are shown in FIG. 3 panel B. The results indicate that the major bcl-X mRNA that is upregulated by CD28 costimulation is bcl-X$_L$. A small induction is also seen in levels of bcl-X$_S$.

Thus, the results of this example indicate that costimulation of activated T cells through CD28 results in a significant increase in bcl-X$_L$ mRNA.

Example 4

T Cells Display Constitutive Expression of Bcl-2 Protein

Since it has been previously reported that the levels of bcl-2 mRNA do not correlate well with the levels of Bcl-2 protein (Chleq-Dechamps, C. M. et al. (1993) *Blood* 81:293–298), the amount of Bcl-2 protein in activated T cells costimulated or not with anti-CD28 was determined.

For this example, CD28+T cells were cultured as indicated above for 0, 6, 12, or 24 hours with anti-CD3 or anti-CD3 and anti-CD28 antibodies and the level of bcl-2 protein determined by immunoprecipitation and Western blot analyses. At each timepoint, 4×10$^7$ cells from each of the culture conditions were isolated and lysed in 1.0 ml NET-N (100 mM NaCl, 1 mM EDTA 20 mM Tris, pH 8.0, 0.2% NP-40). Nuclei and debris were spun out for 2 min in a microcentrifuge at 4° C. The supernatant was then precleared for 30 min with 50 ml Pansorbin (Calbiochem). Following removal of the Pansorbin by centrifugation, the supernatant was split into two equal volumes (450 µl) to which either 1 µl of anti-bcl-X rabbit serum (see Example 5), or 2.5 µg of the hamster anti-Bcl-2 monoclonal 6C8 (Hockenbery, D. et al. (1990) *Nature* 348:334–336) was added. The lysates were rocked at 4° C. for 1 hr prior to the addition of 25 µl of protein A agarose (Gibco BRL) for an additional 30 min. The immunoprecipitates were pelleted and washed twice with NET-N and once with NET. One hundred µliters of 2×SDS loading buffer was added to the pellet which was snap frozen and kept at −20° C. until the gel electrophoresis was performed.

Immunoprecipitations were boiled and subjected to SDS-PAGE, through 15% gels. Gels were transferred to nitrocellulose by electroblotting using the BioRad transfer apparatus at 200 mA for 3 hr. Blots were blocked overnight at 4° C. in 5% nonfat milk/ 0.2% Tween 20 and hybridized with purified 6C8 mAb (1:200) in the blocking solution described above. Western blots were developed using the ECL system (Amersham) with Hyperfilm (Amersham).

Figure 4:
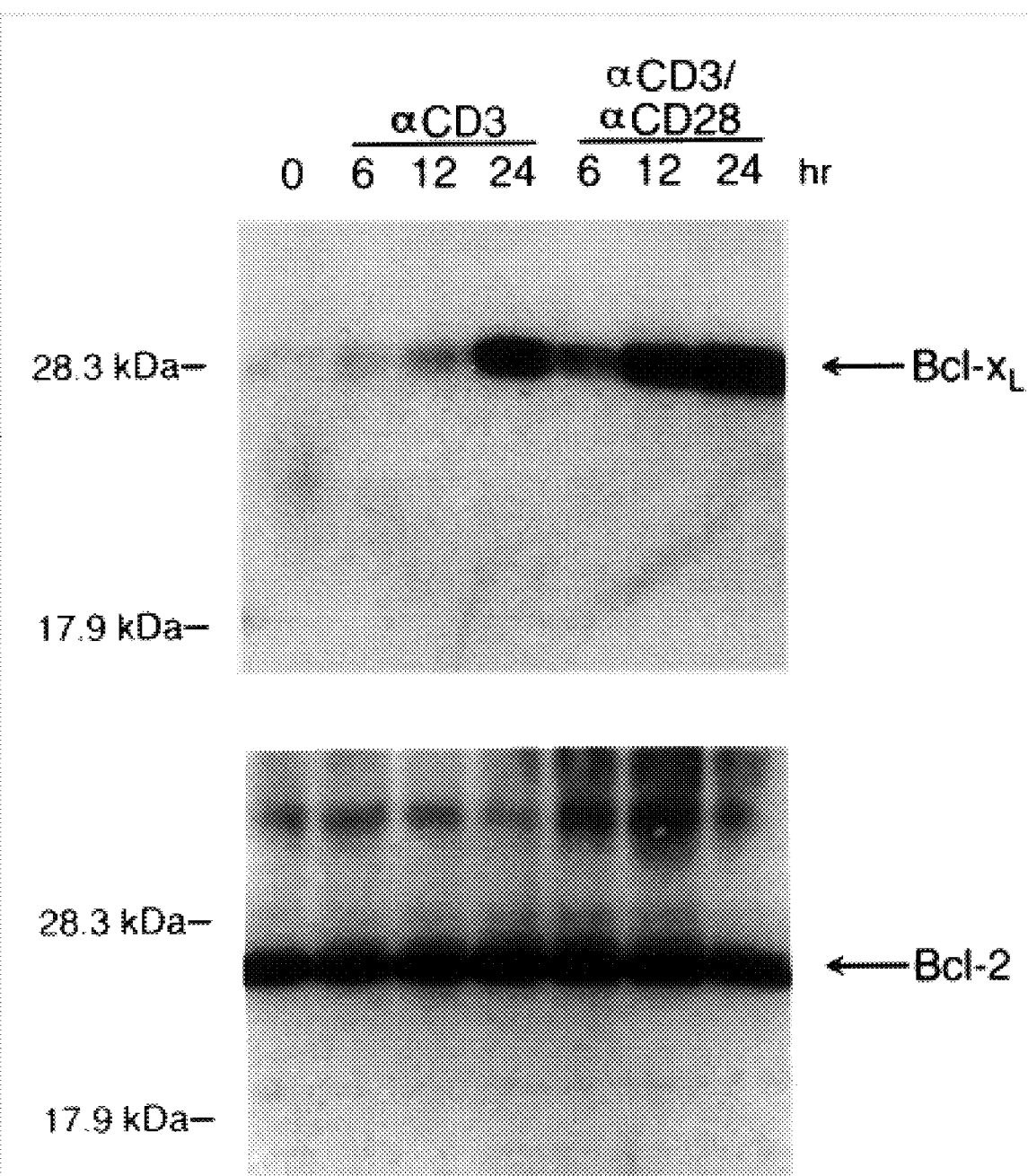
FIG. 4 is a photograph of a Western blot showing the amount of bcl-$X_L$ and Bcl-2 protein in T cells incubated alone (o) or with anti-CD3 (αCD3) for 6, 12, or 24 hours or with anti-CD3 and anti-CD28 (αCD3+αCD28) for 6, 12, or 24 hours.

The results of the Western blot are presented in FIG. 4. It can be seen that resting peripheral blood T cells expressed high levels of Bcl-2 protein. Furthermore, the levels of Bcl-2 protein do not vary significantly over the first 24 hours following TCR/CD3 receptor crosslinking with an anti-CD3 antibody. Costimulation through the CD28 receptor also appeared to have no affect on Bcl-2 protein levels.

This Example shows that resting T cells express bcl-2 protein and that stimulation of the T cells through the T cell receptor with or without costimulation does not increase the level of bcl-2 protein.

Example 5

CD28 Costimulation Enhances bcl-$X_L$ Protein Expression

In this example, the protein level of bcl-$X_L$ in resting T cells or T cells activated through the T cell receptor in the presence or absence of costimulation through CD28, was analyzed.

Protein level of bcl-$X_L$ was determined in the assay described in Example 4 in parallel to determination of Bcl-2 protein levels. In fact, following preclearing, the supernatant was split into two equal volumes (450 µl) and 1 µl of anti-bcl-X rabbit serum was added to one of these aliquots. Protein levels were determined as described in Example 4 using the monoclonal anti-bcl-X antibody 2A1 (1:10 dilution).

Polyclonal and monoclonal antibodies against bcl-X were prepared as follows. The open reading frame of bcl-$X_S$ was amplified by PCR with the primers (5'-GGA GAT ATA CAT ATG TCT CAG AGC AAC CGG GAG CTG GTG-3' (SEQ ID NO:3) and 5'-CGG GAT CCC GTC ATT TCC GAC TGA AGA GTG AGC CCA GCA G-3' (SEQ ID NO:4)) and cloned into the NdeI and BamHI sites of pET-3b (Novagen). Recombinant protein was produced in BL21 cells by induction with 0.4 mM IPTG. This protein was determined to be in the insoluble fraction of a lysis of the bacteria and was partially purified in this manner. The insoluble fraction was washed with 2M urea and solubilized with 6M guanidine-HCL. The protein was renatured by a step dialysis through 3M and 1M guanidine-HCL followed by dialysis against PBS, pH 8.3, with 500 mM KCl. Protein concentration was determined by Bradford assay with a commercially available kit (BioRad) and protein purity was assessed by SDS-PAGE and coomassie blue staining.

For production of rabbit polyclonal antibodies, 1 mg of recombinant protein was suspended in complete Freund's adjuvant (CFA) and injected subcutaneously into multiple sites on the rabbit's back. Animals were boosted with 200 µg of protein in incomplete Freund's adjuvant. Sera were screened by Western blot against recombinant protein and for specific immunoprecipitation using in vitro translated proteins and transfected cell lines.

For production of monoclonal antibodies, BALB/C mice were immunized with recombinant bcl-$X_S$ in polyacrylamide gel emulsified in CFA injected subcutaneously in the hind footpads and intraperitoneally. Mice were boosted twice at 30 day intervals with a mixture of soluble and acrylamide embedded gel-bound protein emulsified in incomplete Freund's adjuvant. Three days after the final boost, spleen and lymph node cells were harvested and fused to P3X63-Ag8.653 myeloma cells using standard techniques (Kearney, J. F. (1984) *In Fundamental Immunology*, W. E. Paul, ed., Raven Press, N.Y., 751–766). Fourteen days after fusion hybridoma supernatants were tested for activity by ELISA on wells coated with recombinant bcl-$X_S$ at 5 µg/ml in borate-buffered saline (pH 8.4). Hybridoma supernatants that were positive by ELISA were screened by Western blot against FL5.12 transfected with bcl-$X_L$ or bcl-2. Positive hybridoma lines were cloned by limiting dilution, rescreened and then injected into pristane-primed BALB/c mice for ascites production.

The results of the Western blot analysis showing protein levels of bcl-X is indicated in FIG. 4. bcl-X protein levels varied significantly with the level of T cell activation. No detectable bcl-X protein products were observed in resting peripheral blood T cells. The protein recognized by the antibodies on the Western blot corresponds to bcl-$X_L$ and not to bcl-$X_S$ since in vitro translated bcl-$X_L$ as well as bcl-$X_L$ protein synthesized in cell transfected with the corresponding cDNA is approximately 29 kDa in size, while bcl-$X_S$ protein is approximately 21 kDa (Boise, L. H. et al. (1993) *Cell* 74:597–608).

FIG. 4 further indicates that anti-CD3 stimulation of resting T cells induces the expression of detectable bcl-$X_L$ protein that was first observed 6 hours following stimulation and accumulated in the cell throughout the 24 hour period of analysis. Moreover, CD28 costimulation of anti-CD3 stimulated cells significantly enhanced expression of bcl-$X_L$ protein. At no time was bcl-$X_S$ protein observed.

In another example, resting T cells were activated for 24 hours with medium alone, anti-CD28, anti-CD3, anti-CD3 and anti-CD28, or anti-CD3 and IL-2 (100 u/ml). Cytoplasmic extracts were prepared as described and 100 µg of protein were subjected to SDS-PAGE and Western blot analysis with a polyclonal bcl-X serum.

Figure 5:
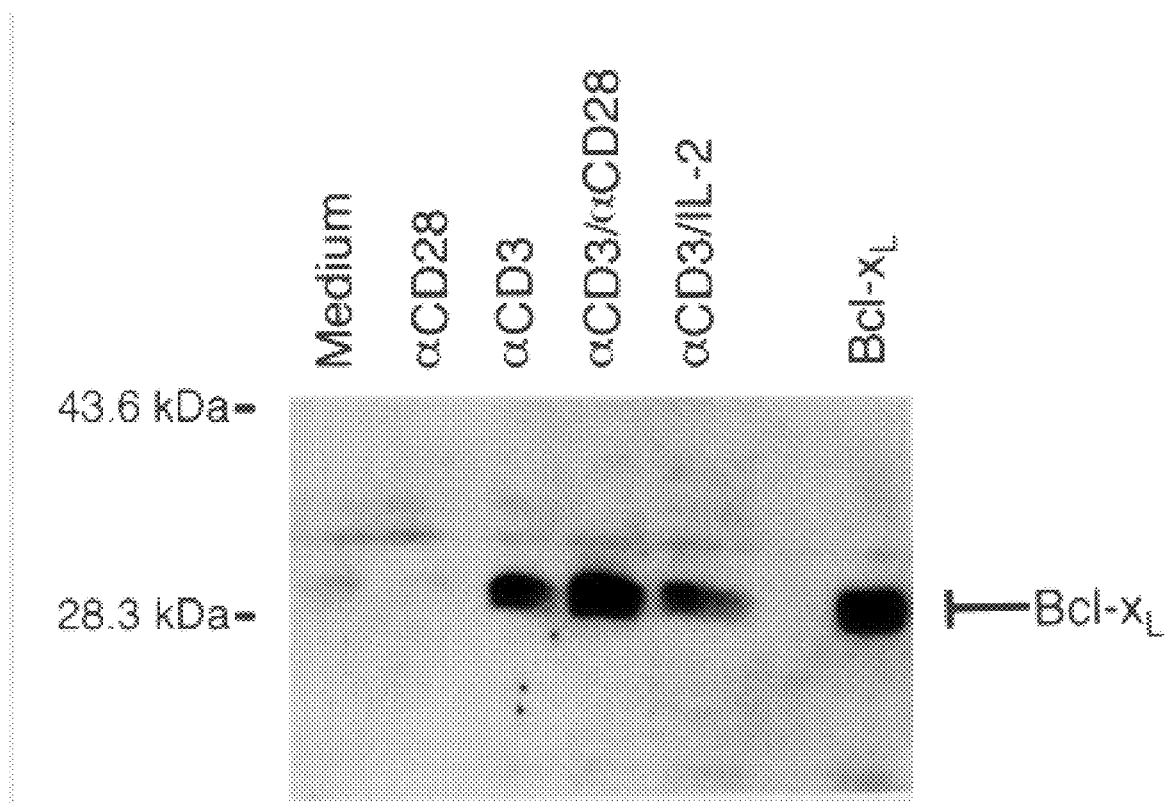
FIG. 5 is a photograph of a Western blot showing the amount of bcl-$X_L$ protein in T cells incubated for 24 hours in medium alone (Medium), or in the presence of anti-CD28 (αCD28), anti-CD3 (αCD3), anti-CD3+anti-CD28 (αCD3/αCD28), or anti-CD3+IL-2 (100 units/ml) (αCD3/IL-2).

The results, which are represented in FIG. 5, indicate that resting T cells as well as T cells incubated with anti-CD28 failed to express bcl-$X_L$ protein. However, CD28 costimulation of anti-CD3-stimulated cells significantly enhanced the expression of bcl-$X_L$ protein (FIGS. 4 and 5). The levels of expression of bcl-$X_L$ in anti-CD3+anti-CD28 stimulated cells at 24 hours were similar to those obtained in stable transfectants in which bcl-$X_L$ is being expressed under control of the spleen focus-forming virus long terminal repeat (last lane of FIG. 5).

CD28 costimulation resulted in enhancement of bcl-$X_L$ protein accumulation observable as early as 6 hours following stimulation and continuing throughout the 24 hour period of culture (FIGS. 4 and 5). In contrast, treatment of cells with anti-CD3 and IL-2 (100 units/ml) does not further enhance bcl-$X_L$ expression above the levels seen in T cells treated with anti-CD3 alone (FIG. 5). Furthermore, treatment of anti-CD3-activated T cells with monoclonal antibodies to CD2, CD5, CD11a, CD18 or to MHC class I does not enhance bcl-$X_L$ levels above that of cells treated with anti-CD3 alone.

These results indicate that resting T cells do not express bcl-$X_L$ protein, T cells activated with anti-CD3 express bcl-$X_L$ protein, and T cells activated with anti-CD3 and costimulated with anti-CD28 express significantly more bcl-$X_L$ protein.

Example 6 bcl-$X_L$ Prevents Fas- and Anti-CD3-induced PCD in Jurkat T Cells

Crosslinking of Fas on T cell lines results in the rapid induction of apoptosis. However, normal T cells do not become susceptible to cell death in response to Fas-crosslinking until they have been activated for extended periods of time (Klas, C. et al. (1993) *Int. Immunol.* 5:625–630). Cells are rapidly induced to express high levels of Fas on the cell surface within 24 hours of activation with anti-CD3+anti-CD28. Fas levels then remain constant for the next several days in culture. Despite this, the ability of Fas-crosslinking to induce apoptosis does not become apparent until 72 hours after stimulation and then becomes increasingly more effective over the next several days in culture. This example demonstrates that bcl-$X_L$ protein level in T cells stimulated with anti-CD3 and anti-CD28 correlates with resistance to Fas-induced cell death.

Figure 6:
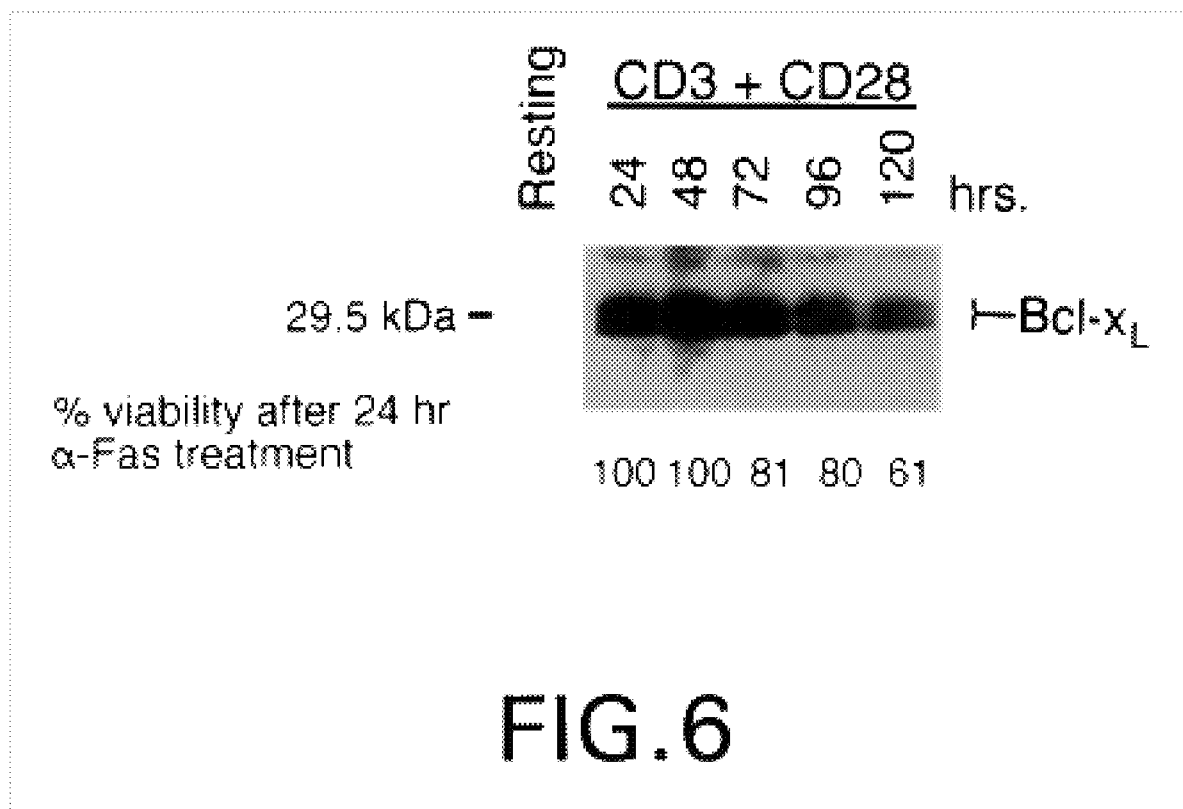
FIG. 6 is a photograph of a Western blot showing the amount of bcl-$X_L$ protein in T cells incubated in medium alone (Resting) or incubated for 24, 48, 72, 96, or 120 hours in the presence of anti-CD3 and anti-CD28 antibodies. The lower panel indicates the percent viability of T cells incubated in medium alone (Resting) or incubated for 24, 48, 72, 96, or 120 hours in the presence of anti-CD3 and anti-CD28 antibodies followed by the addition of anti-Fas antibody for an additional 24 hours.
Figure 7A:
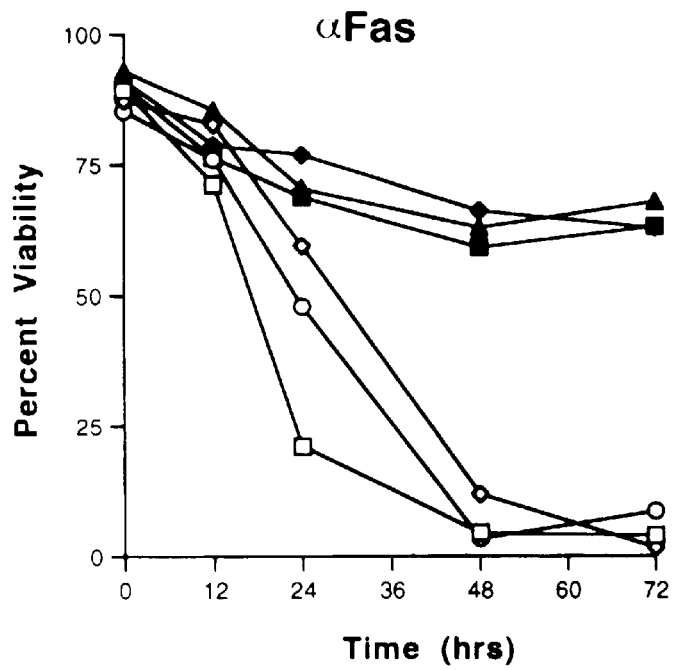
FIGS. 7 A–B are graphical representations of the percent survival of Jurkat clones transfected with a bcl-$X_L$ expression plasmid (bcl-$X_L$ clones 1, 2, and 3) or control plasmid Neo clones 1, 2, and 3) after 0, 12, 24, 48, and 72 hours of treatment with anti-Fas antibody (αFas, panel A) or anti-CD3 antibody (αCD3, panel B).
Figure 7B:
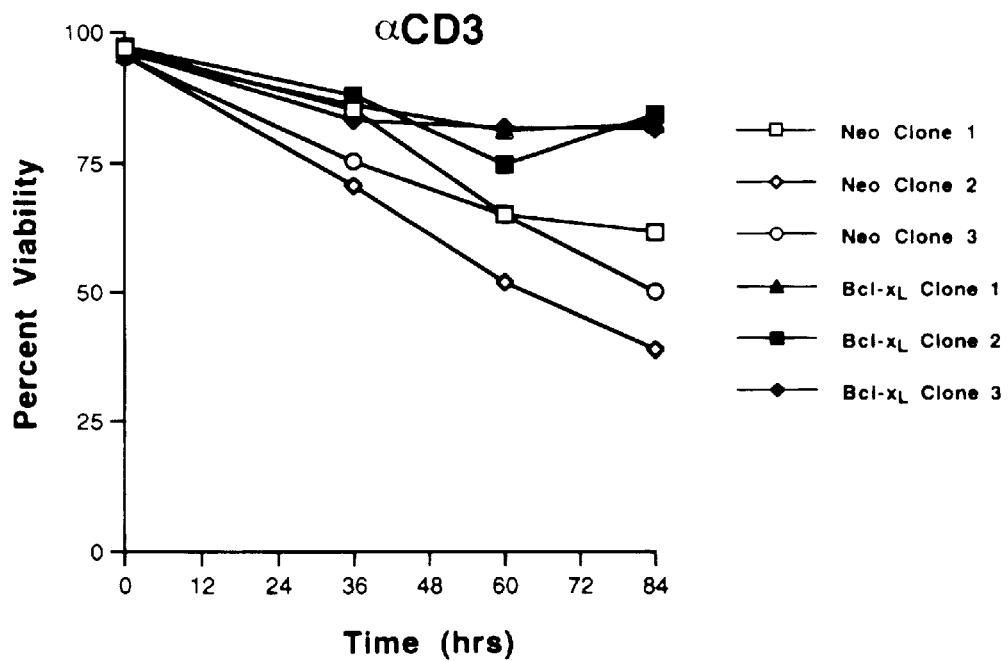
Figure 7C:
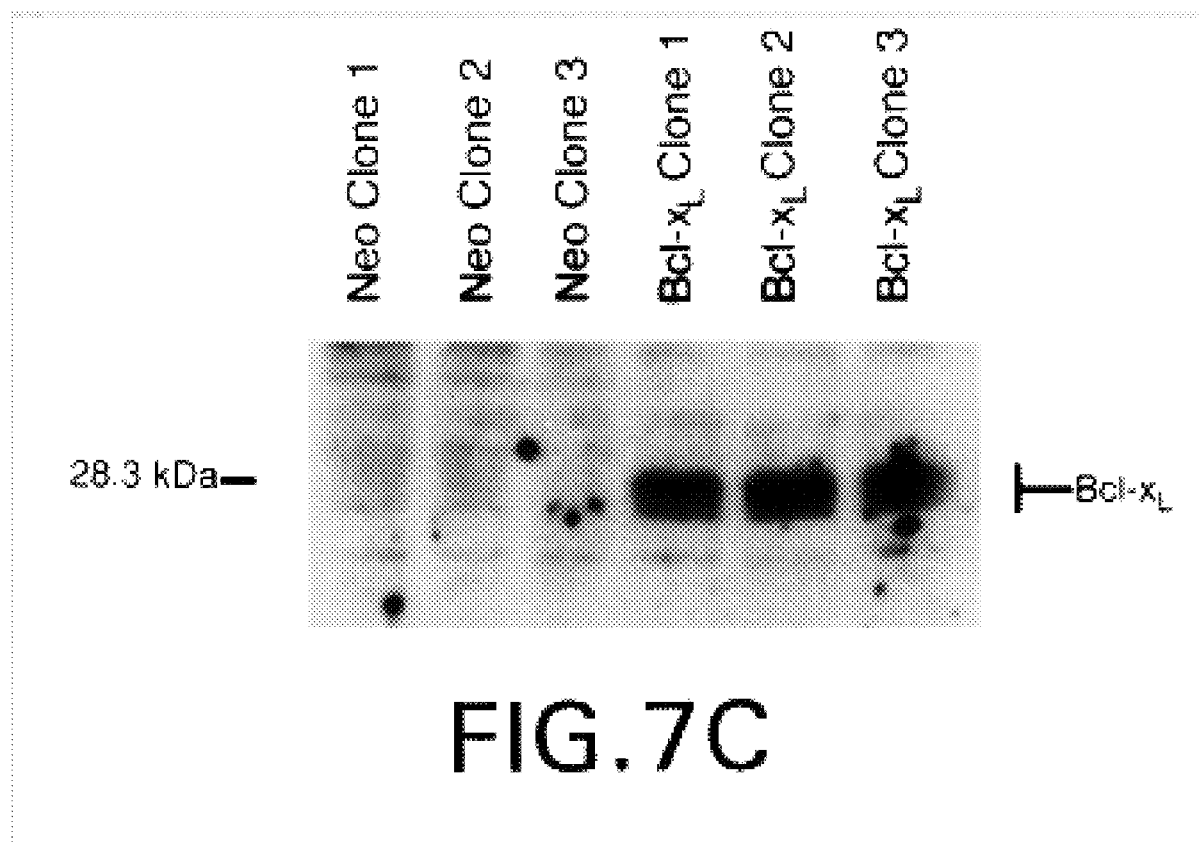
Figure 7D:
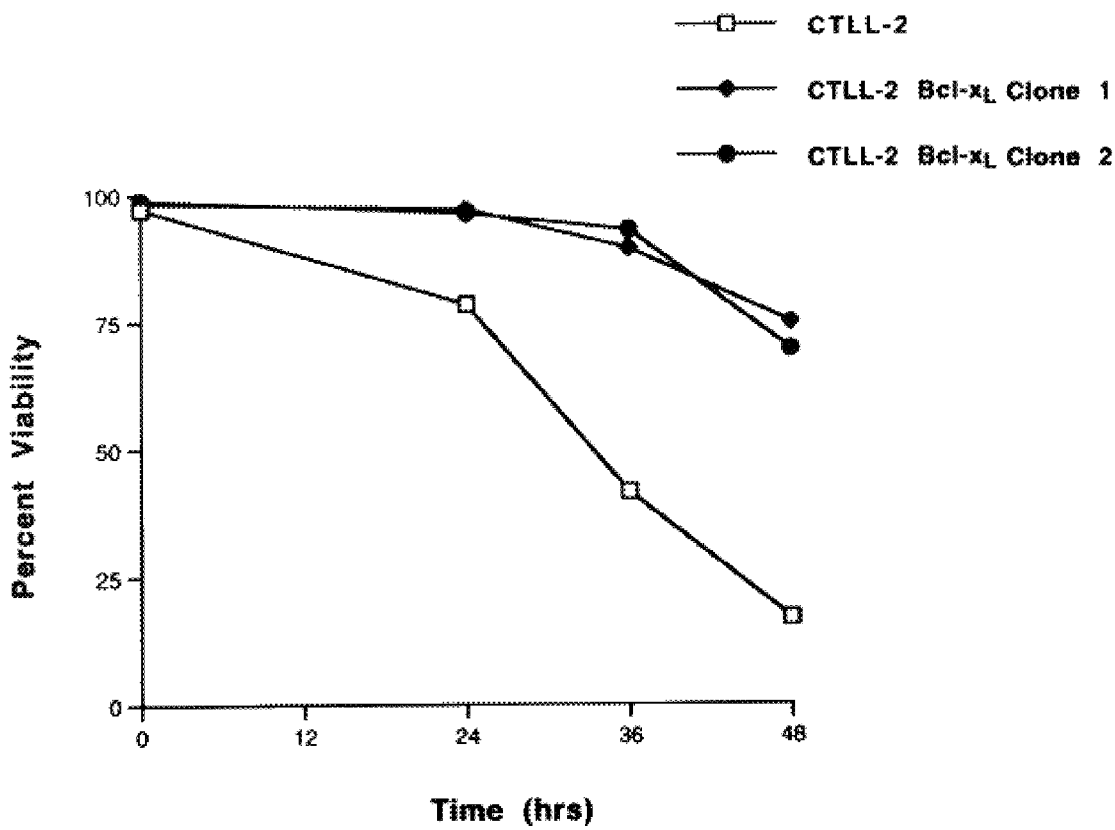
Figure 7E:
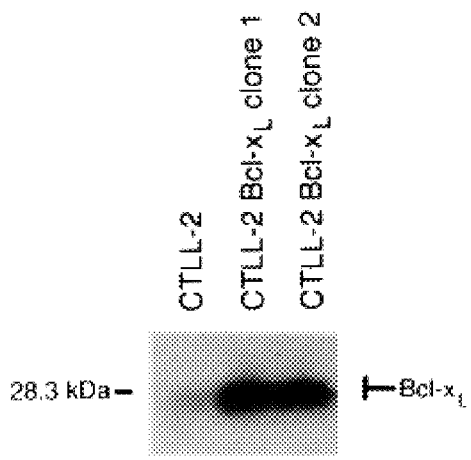

T cells were activated with medium alone or anti-CD3 and anti-CD28 for a 120 hour time course. Cytoplasmic lysates were prepared and analyzed by Western blot staining with the polyclonal anti-bcl-$X_L$ antibody, as described above. At the same time, anti-CD3 and anti-CD28 stimulated T cells were treated with 0.5 µg/ml CH-11 anti-Fas monoclonal antibody (Panvera) or an isotype control (IgM) for 24 hours at each 24 hours interval of the 120 hour timecourse. Viability was assessed by propidium iodide exclusion as described above. Fas surface expression was confirmed by staining with CH-11, for 30 minutes followed by FITC-conjugated anti-mouse IgM (Sigma) for 30 minutes. Stained cells were analyzed by flow cytometry (FACSort, Becton-Dickinson) utilizing Lysis II software.

bcl-$X_L$ protein levels and viability of the T cells crosslinked with anti-Fas antibody are represented in FIG. 6. Following anti-CD3+anti-CD28 costimulation, the peak of bcl-$X_L$ protein expression was between 24 and 48 hours and declined progressively thereafter. As indicated in the lower half of the figure, cells treated for 24 or 48 hours with anti-CD3 and anti-CD28 and then crosslinked with Fas are completely resistant to cell death. However, when the T cells were crosslinked with anti-Fas antibody at later timepoints following stimulation with anti-CD3 and anti-CD28, cell viability declined. Thus, the presence of bcl-$X_L$ protein correlates with protection of the T cells against Fas induced cell death.

To further demonstrate that bcl-$X_L$ protein induces resistance to Fas-crosslinking induced cell death, Jurkat T cells were transfected with an expression vector encoding bcl-$X_L$ and cell viability determined following addition of anti-Fas antibody.

Jurkat cells were maintained in medium as described above and transfected with pSFFVNeo-bcl-$X_L$ (Boise, L. H. et al. (1993) *Cell* 74:597–608) or pSFFVNeo by electroporation with a Gene Pulser (BioRad) at 250 V and 960 µF. Transfectants were selected with G418 (Sigma) at 1 mg/ml and several independent clones were isolated by limiting dilution. Western blot analysis indicated that high bcl-$X_L$ protein levels are present in clones transfected with the bcl-$X_L$ expression vector, and that clones transfected with the control vector (Neo clones) do no express bcl-$X_L$ protein (FIG. 7, panel C). bcl-$X_L$ levels in the bcl-$X_L$-transfectants were comparable to the levels expressed in T cells 24 hours after anti-CD3+anti-CD28 costimulation (see FIG. 5 for example). Fas expression on clones was confirmed by staining as described above.

Three bcl-$X_L$ and three Neo clones which expressed comparable levels of Fas on their surface were incubated in medium at 2.5×10$^5$ cells/ml, treated with Fas antibody at 10 ng/ml or an isotype matched control and viability was assessed over time by propidium iodide exclusion. The percent viability of the Jurkat cell clones is indicated in FIG. 7, panel A. The graph indicates that Fas induced rapid cell death in all three control transfectants (less than 10% viability at 48 hours), while the three bcl-$X_L$-transfectants remain greater than 60% viable throughout the experiment. Neither the neo- nor the bcl-$X_L$-transfectants demonstrated decreases in viability when no antibody or an isotype matched control mAb (IgM) was used. Thus, bcl-$X_L$ substantially blocks Fas-induced cell death in Jurkat cells.

Anti-CD3-crosslinking has also been reported to induce apoptosis in T cell clones and cell lines (Shi, Y. et al. (1989) *Nature* 339:625–626), Ucker, D. S. et al. (1989) *J. Immunol.* 143:3461–3469). To examine the ability of bcl-$X_L$ to prevent TCR induced cell death, the Jurkat transfectants were stimulated with anti-CD3 and their survival followed. Anti-CD3-induced cell death was performed with plate bound anti-CD3 (OKT3) at 1 µg/ml and viability assessed daily by propidium iodide exclusion.

The results are presented graphically in FIG. 7, panel B. By 84 hours, anti-CD3 treatment had resulted in 30–60% cell death in the cultures of Neo clones. In contrast, anti-CD3-induced cell death was almost completely inhibited by the presence of bcl-$X_L$. (FIG. 7, panel B).

Thus, bcl-$X_L$ protein is capable of protecting T cells from Fas- and T cell receptor crosslinking induced cell death.

Example 7 bcl-$x_L$ Can Function Independently of IL-2 to Enhance T Cell Survival

Based on the analyses of the effect of IL-2 on the survival of T cells activated through crosslinking of the TCR/CD3 complex, it appears that IL-2 can function as a survival factor in maintaining the viability of antigen-activated T cells. Although it appears that CD28 costimulation results in T cell survival that is independent of the growth factor levels in the supernatant, it is difficult to rule out that the enhanced survival of CD28 stimulated cells was not merely the result of the high levels of IL-2 produced by CD28 costimulation. The high levels of IL-2 produced in CD28-costimulated cells may make it impossible to completely eliminate the effects of lymphokines by serial washing. The high levels of lymphokine produced by CD28-costimulated cells could potentially affect the cells in an autocrine fashion even in the absence of detectable lymphokine accumulation in cultured supernatants. This example demonstrates that bcl-$X_L$ protein is capable of protecting an IL-2-dependent T cell line from undergoing PCD upon IL-2 withdrawal.

CTLL-2 is a T cell line whose survival and proliferation in culture is dependent on IL-2 (Gillis, S. and Smith, K. A. (1977) *Nature* 268:154–156). These cells can not be induced to secrete their own IL-2 and are frequently used in bioassays for IL-2. CTLL-2 cells were maintained in the growth medium described above with addition of β-mercaptoethanol (50 µM) and recombinant IL-2 (100 units/ml) (Nuñez, G. et al. (1990) *J. Immunol.* 144:3602–3610). Cells were transfected with the expression vector pSFFVNeo-bcl-$X_L$ (Boise, L. H. et al. (1993) Cell 74:597–608) by electroporation with a Gene Pulser (BioRad) at 250 V and 960 µF. Transfectants were selected on 250 µg/ml G418, and bcl-$X_L$ positive clones were identified by Western blot analysis. CTLL-2 cells (2.5×10$^6$) were lysed in 50 ml of NET-N and the nuclei and debris removed as described above. Fifty µl of 2×SDS loading buffer was added to the supernatant and SDS-PAGE and Western blotting was performed as described above.

Two bcl-$X_L$ clones expressing high levels of bcl-$X_L$ protein (FIG. 7 panel E) were tested for their ability to survive in culture in the absence of IL-2. These clones expressed bcl-$X_L$ at levels similar to that of anti-CD3+anti-CD28 activated T cells. The bcl-$X_L$ expressing cells were plated in fresh medium at $3\times10^5$ cells/ml one day prior to deprivation. Cells were then washed 3 times in fresh medium without IL-2 and resuspended in the same medium. Viability was assessed by propidium iodide exclusion on indicated days. The results are presented graphically in FIG. 7 panel D. Both bcl-$X_L$-transfected clones had enhanced survival in the absence of IL-2 when compared to the parental cell line (FIG. 7, panel D). Thus, bcl-$X_L$ can function in the absence of IL-2 to enhance T cell survival. These clones were also tested for radiation-induced death in assays similar to the assays presented in FIG. 2. Clones expressing bcl-$X_L$ displayed significant protection from radiation-induced death when compared to control cells tested either in the presence or absence of IL-2.

Thus, this example demonstrates that bcl-$X_L$ protein protects T cells from cell death induced by IL-2 deprivation.

Example 8

Expression of bcl-$x_L$ via CD28 Costimulation is Evolutionarily Conserved

To determine if the ability of CD28 costimulation to regulate bcl-$X_L$ expression is conserved between mouse and human, cells isolated from murine lymph nodes were activated with soluble anti-CD3 and bcl-$X_L$ expression assessed.

Lymph nodes were harvested from C57BL/6 mice (Jackson laboratories) and single cell suspensions were prepared by passage through nylon mesh. Cells were plated at $2\times10^6$/ml in complete medium consisting of DMEM (GIBCO BRL) supplemented with 10% fetal calf serum, penicillin (100 U/ml), streptomycin (100 U/ml), 10 mM HEPES, 50 mM β-ME and 0.1 mM nonessential amino acids. Soluble anti-CD3 (145-2C11, 10 µg/ml from J. Bluestone) was added alone or in combination with anti-CD28 (10 µg/ml) or CTLA4Ig (100 µg/ml, from Repligen). Cultures were incubated for 24 hours at 37° C., 7% $CO_2$ and harvested for Western blot analysis. Murine lymphocytes ($5\times10^6$) were lysed in 50 µl of NET-N and the nuclei and debris removed as described above. Fifty µl of 2×SDS loading buffer was added to the supernatant and SDS-PAGE and Western blotting was performed as described above. For viability studies cells were treated as described above. Viability of T cells following activation was assessed by propidium iodide exclusion of Thy-1 positive cells.

Figure 8:
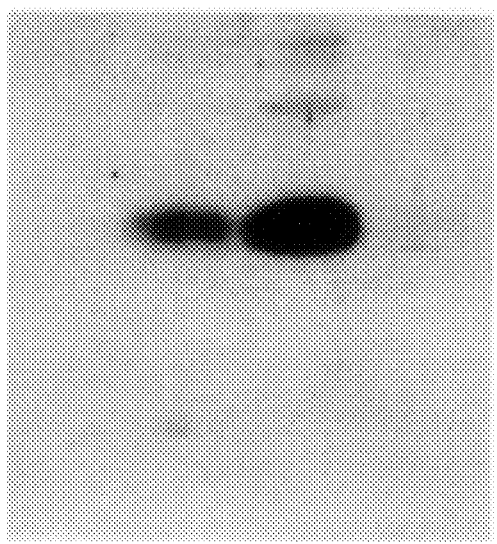
FIG. 8 is a photograph of a Western blot showing the amount of bcl-$X_L$ protein in mouse lymph node cells incubated for 24 hours in medium alone, in the presence of anti-CD3, in the presence of anti-CD3 and anti-CD28, and in the presence of anti-CD3 and CTLA4Ig.

The results, presented in FIG. 8, indicate that resting murine lymphocytes do not express any detectable bcl-$X_L$, as is the case with human T cells (FIG. 8, lane 1). Soluble anti-CD3 treatment for 24 hours induced bcl-$X_L$ expression in T cells when accessory cells are present to deliver a costimulatory signal. This level of bcl-$X_L$ was enhanced if this costimulatory signal was amplified by addition of anti-CD28. In contrast, the ability of soluble anti-CD3 to upregulate bcl-$X_L$ expression in the presence of accessory cells is almost completely inhibited by the addition of CTLA4Ig, a reagent which prevents CD28 costimulation by competitively inhibiting the CD28 ligands B7-1 and B7-2 from interacting with CD28. These data demonstrate that in mouse T cells bcl-$X_L$ expression is also induced during cell activation. Furthermore, at submitogenic doses of anti-CD3, the induction of bcl-$X_L$ expression is almost completely dependent on CD28 costimulation. This expression pattern demonstrates that bcl-$X_L$ plays a role in activated T cell survival in the mouse. Consistent with this possibility, the viability of Thy-1 positive cells from the unseparated lymph node cell population stimulated with anti-CD3 alone was 62% after 72 hours. In contrast, the addition of anti-CD28 enhances the viability of the Thy-1 positive cells to 88%. Conversely, by blocking CD28/B7 mediated costimulation within the lymph node cells with CTLA4Ig, viability of the activated T cells is reduced to 20% at 72 hrs.

This example thus shows that bcl-$X_L$ has the same pattern of expression in mouse T cells as in human T cells, i.e., bcl-$X_L$ protein is absent from resting T cells, bcl-$X_L$ protein is expressed in T cells activated through crosslinking of the T cell receptor, and bcl-$X_L$ protein level is further increased upon costimulation through CD28.

Example 9 bcl-$X_L$ Expression Can Prevent HIV-I -induced Cell Death

To determine whether bcl-$X_L$ expression protects T cells from HIV-1 - induced cell death, the Jurkat cell clones transfected with pSFFVNeo-bcl-$X_L$ (bcl-$X_L$) or with the vector alone (Neo) described above were infected with HIV and viability determined.

Three Jurkat cell clones transfected with the bcl-$X_L$ expression vector and three Jurkat cell clones transfected with the control vector were infected with various dilutions of cell-free viral stock of HIV-RF isolate. On day 12 after infection cell death was quantified by a tetrazolium/formazan assay (See Shearman, M. S. et al. (1994) *Proc. Natl. Acad. Sci. USA* 91:1470–1474; Hansen, M. B. et al. (1989) *J. Immun. Methods* 119:203–210).

Figure 9:
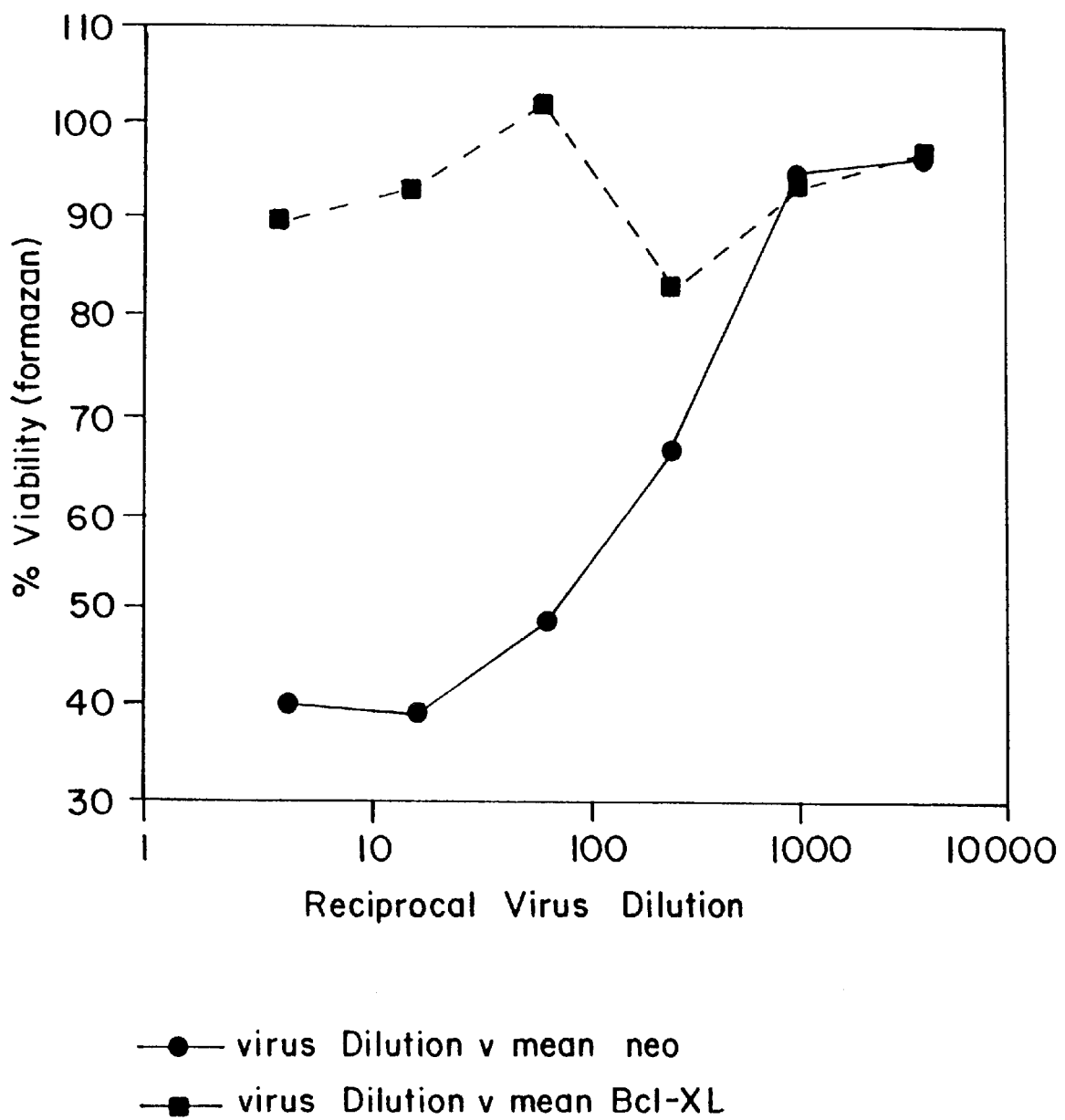
FIG. 9 is a graphic representation of the percent viability of Jurkat cells transfected with a bcl-$X_L$ expression vector (virus Dilution v mean bcl-$X_L$) or with a control vector (virus Dilution v mean neo) and infected with various amounts of HIV.

The mean viability of the three cell lines is represented graphically in FIG. 9. Control Jurkat cells had a high degree of cell death when infected with virus stock at dilutions of 1:4 to 1:256. In contrast, the transfected Jurkat cells that expressed the bcl-$X_L$ gene did not have any impairment in viability over these same virus dilutions.

To determine whether the protective effect of bcl-$X_L$ expression was due to resistance to HIV-1 infection, or to a more specific effect on the induction of cell death, the amount of virus in the supernatants of the infected cells was quantitated on day 7 post infection by the method of Spearman and Karber. The Spearman-Karber method is described in Richman D. B., Johnson V. A., Mayrs V. L. (1993) In vitro evaluation of experimental agents for anti-HIV activity. *Current Protocols in Immunology* ch. 12.9, Colligan J. E. et al., eds. Greene and Wiley, Interscience N.Y.

The results are shown in Table 1. There was about a four fold decrease in the amount of virus in the supernatant of the bcl-$X_L$ expressing cells as compared to the control cells.

TABLE 1

Amount of HIV particles in the supernatant of cells transfected with bcl-$X_L$ or vector only

| Cell line | TCID50 |
|---|---|
| N1.7 | 2048 |
| N1.8 | 2048 |
| N1.22 | 676 |
| BclX.8 | 512 |
| BclX.10 | 294 |
| BclX.13 | 512 |

The results of these examples indicate that bcl-$X_L$ protein protects T cells from HIV-induced cell death. This effect may be useful in preventing the decline of CD4 cells during HIV infection. The present results also suggests that one mechanism of excess cell death in patients with HIV infection may be that certain forms of T cell activation in these patients fail to induce bcl-$X_L$ expression to levels comparable to that of uninfected individuals. Thus, one means of therapy for HIV infection would be to restore the induction of bcl-$X_L$ expression by ex vivo cell activation and expansion or by in vivo induction of CD28 signal transduction. Alternatively, induction of bcl-$X_L$ expression can be achieved by stimulation with an agent other than an agent that stimulates CD28. These data indicate that the ability of CD28 to enhance bcl-$X_L$ expression has clinical utility in states of immunodeficiency where excess lymphoid cell death occurs, especially in HIV infection where programmed cell death occurs in peripheral blood T cells and in lymph node T cells.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for inhibiting cell death in a virally infected T-cell by increasing the level of bcl-$X_L$ protein in the T-cell, comprising introducing into the T-cell in vitro a nucleic acid molecule comprising a gene encoding a human bcl-$X_L$ protein operably linked to at least one regulatory sequence, wherein the at least one regulatory sequence allows for inducible expression of the bcl-$X_L$ protein in the T-cell, such that T-cell death is inhibited in the virally infected T-cell.

2. The method of claim 1, wherein the T cell is infected with Human Immunodeficiency Virus.

3. A method for inhibiting cell death in a T-cell in a subject by increasing the level of bcl-$X_L$ protein in the T-cell, wherein the T-cell in the subject is infected with a virus, comprising obtaining the T cell from the subject, introducing into the T-cell in vitro a nucleic acid molecule comprising a gene encoding a bcl-$X_L$ protein operably linked to at least one regulatory sequence which allows for inducible expression of the bcl-$X_L$ protein in the T-cell, and reintroducing the T-cell into the subject, such that T-cell death is inhibited in the T-cell of the subject.

4. The method of claim 3, wherein the virus is Human Immunodeficiency Virus.

5. The method of any one of claims 1, 2, 3, or 4, wherein the T-cell is a mammalian T-cell.

* * * * *